Figures 1A, 1B:
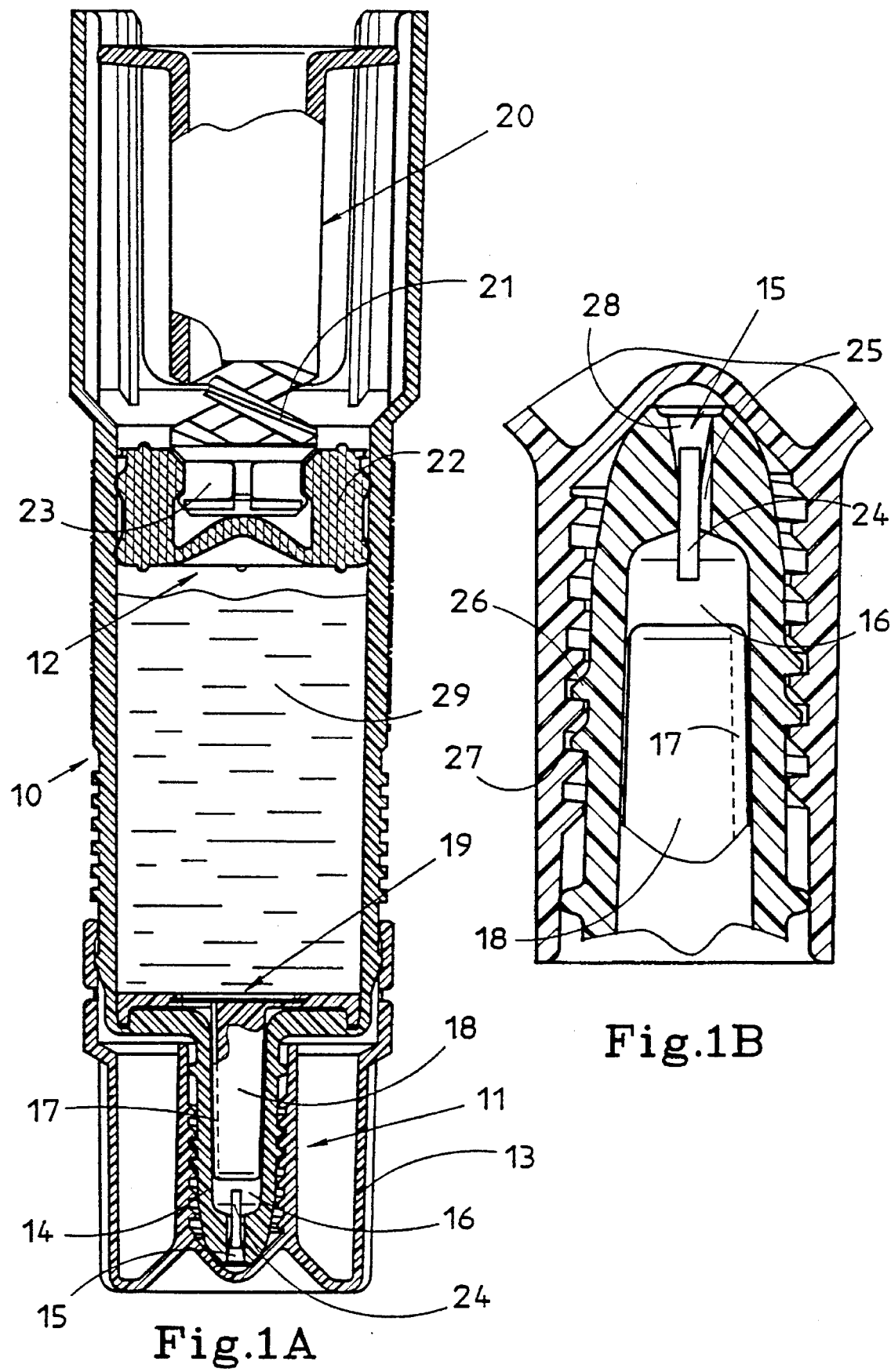

United States Patent [19]
Meyer

[11] Patent Number: 5,499,751
[45] Date of Patent: Mar. 19, 1996

[54] DEVICE FOR STORING A LIQUID MEDICINAL SUBSTANCE AND FOR ADMINISTERING EYE DROPS

[76] Inventor: Gabriel Meyer, La Dullive, CH-1195 Dully, Switzerland

[21] Appl. No.: 119,113

[22] PCT Filed: Jan. 21, 1993

[86] PCT No.: PCT/CH93/00014

§ 371 Date: Oct. 18, 1993

§ 102(e) Date: Oct. 18, 1993

[87] PCT Pub. No.: WO93/13737

PCT Pub. Date: Jul. 22, 1993

[30] Foreign Application Priority Data

Jan. 21, 1992 [FR] France ................................. 92 00728
Jun. 9, 1992 [FR] France ................................. 92 07167

[51] Int. Cl.$^6$ .................................................. B67D 5/42
[52] U.S. Cl. ........................... 222/386; 604/190; 604/301
[58] Field of Search ........................... 222/189, 162, 222/320, 321, 420, 386; 604/190, 218, 231, 265, 256, 301, 311, 295; 128/763

[56] References Cited

U.S. PATENT DOCUMENTS

| | | | |
|---|---|---|---|
| 3,934,585 | 1/1976 | Maurice | 222/420 |
| 4,316,462 | 2/1982 | Baker | 604/190 |
| 4,596,561 | 6/1986 | Meyer et al. | 604/190 |
| 4,638,809 | 1/1987 | Kuperus | 128/763 |
| 4,820,276 | 4/1989 | Moreno | 222/386 |
| 5,056,689 | 10/1991 | Heyl et al. | 222/420 |
| 5,154,710 | 10/1992 | Williams | 604/301 |

FOREIGN PATENT DOCUMENTS

| | | |
|---|---|---|
| 0207544 | 1/1987 | European Pat. Off. . |
| 0439999 | 8/1991 | European Pat. Off. . |
| 2010681 | 7/1979 | United Kingdom . |
| WOA9116868 | 11/1991 | WIPO . |

OTHER PUBLICATIONS

Design Engineering. Aug. 1990, London GB 'eye dispenser for glaucoma treatment' see the whole document.

*Primary Examiner*—Andres Kashnikow
*Assistant Examiner*—Philippe Derakshani
*Attorney, Agent, or Firm*—Davis, Bujold & Streck

[57] ABSTRACT

The device represented in its storage position contains essentially a body (11) in synthetic material containing a reservoir (10) containing a medicinal substance (29). The body (11) is fitted with an applicator nozzle (15). The reservoir (10) has the shape of a cylindrical glass jacket (17) closed at one end by a movable sealing plug (18) and at the other end by a mobile piston (19). The mobile piston is linked with a plunger (16) which advantageously is a spring in a synthetic material. A flow rate controlling filter (19) is lodged in the applicator nozzle (15). This device is advantageous because the reservoir can be sterilized with its contents. The filter and the piston along with the plunger guarantee the medicinal substance remains in an aseptic state by preventing contamination via the applicator nozzle.

9 Claims, 17 Drawing Sheets

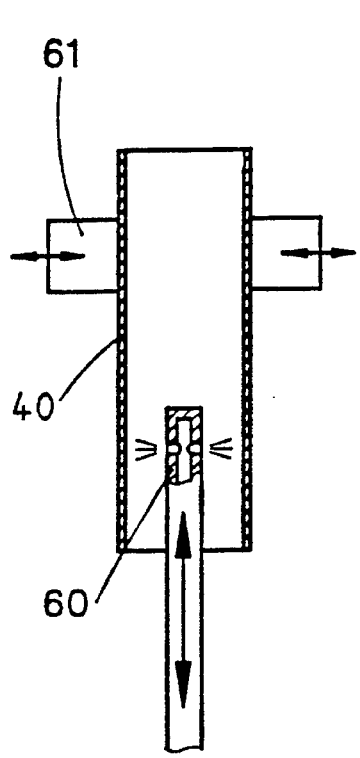
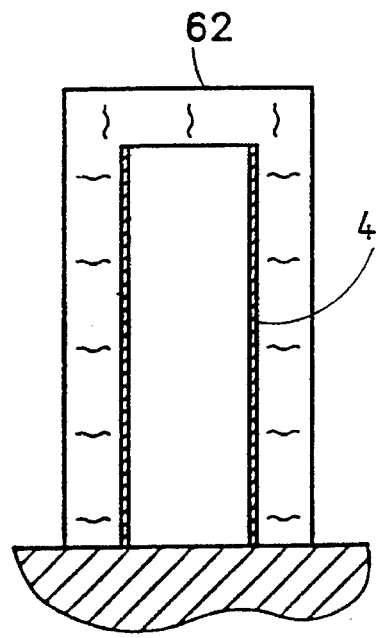
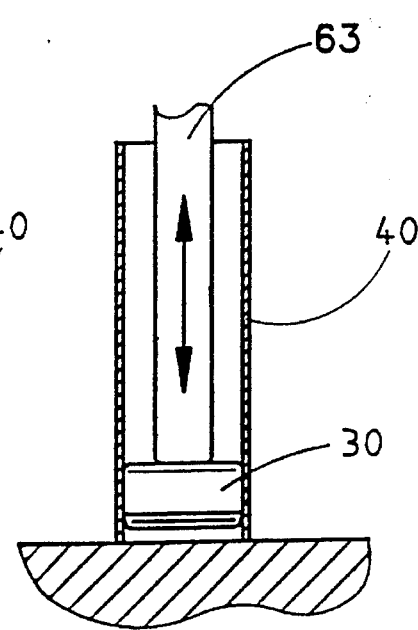
Fig.12     Fig.13     Fig.14
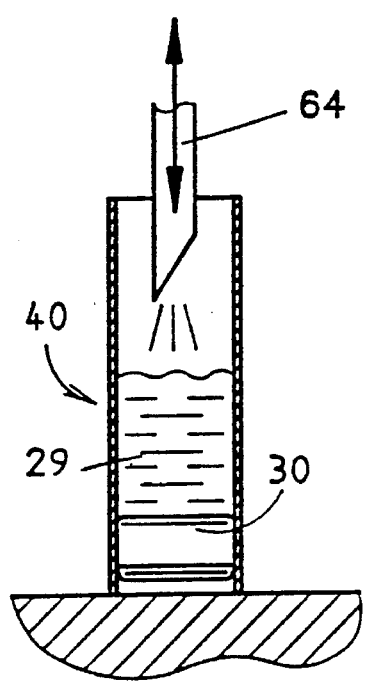
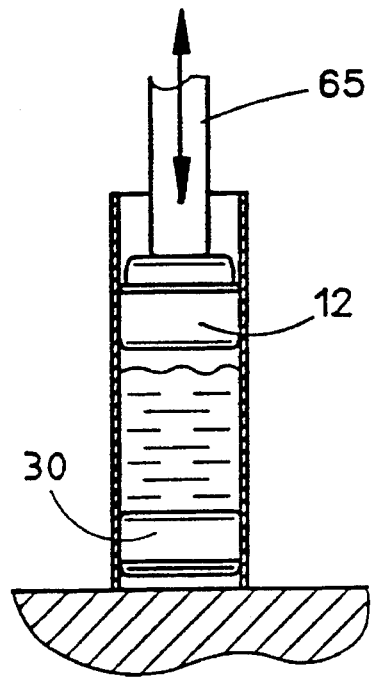
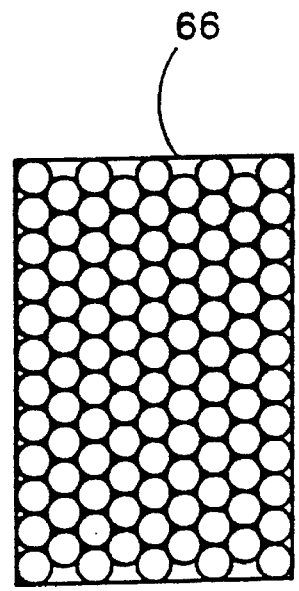
Fig.15     Fig.16     Fig.17

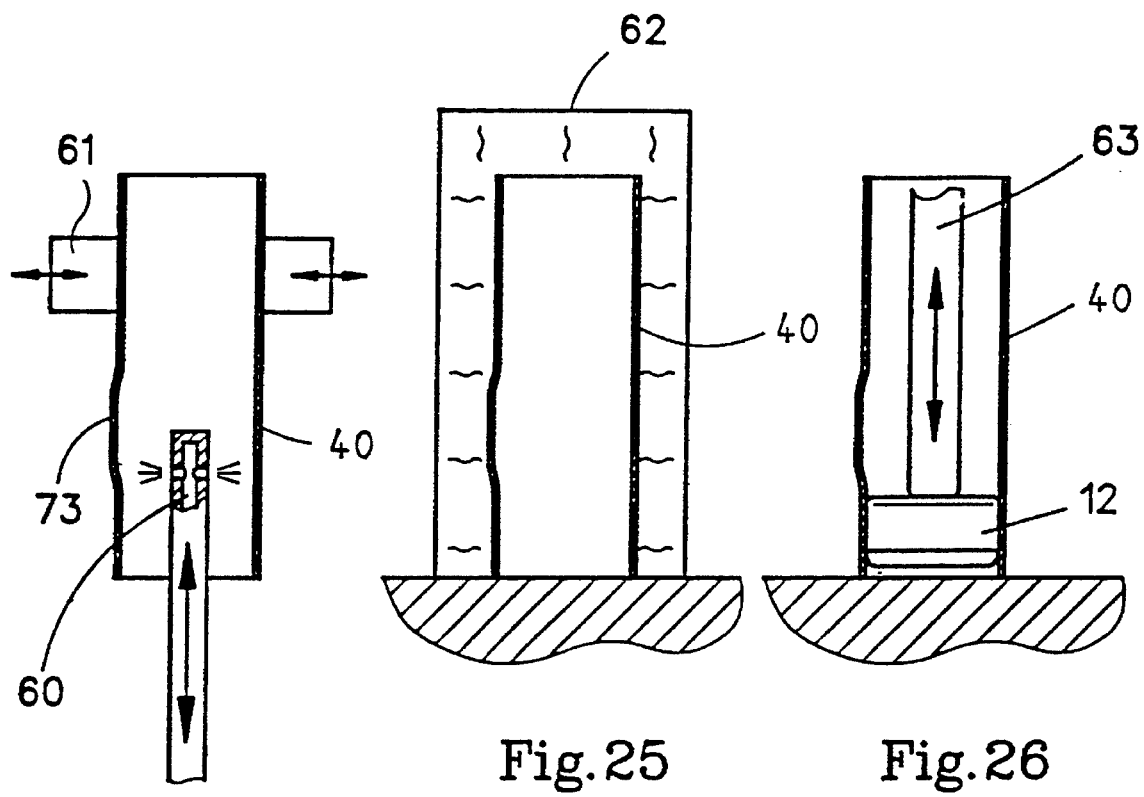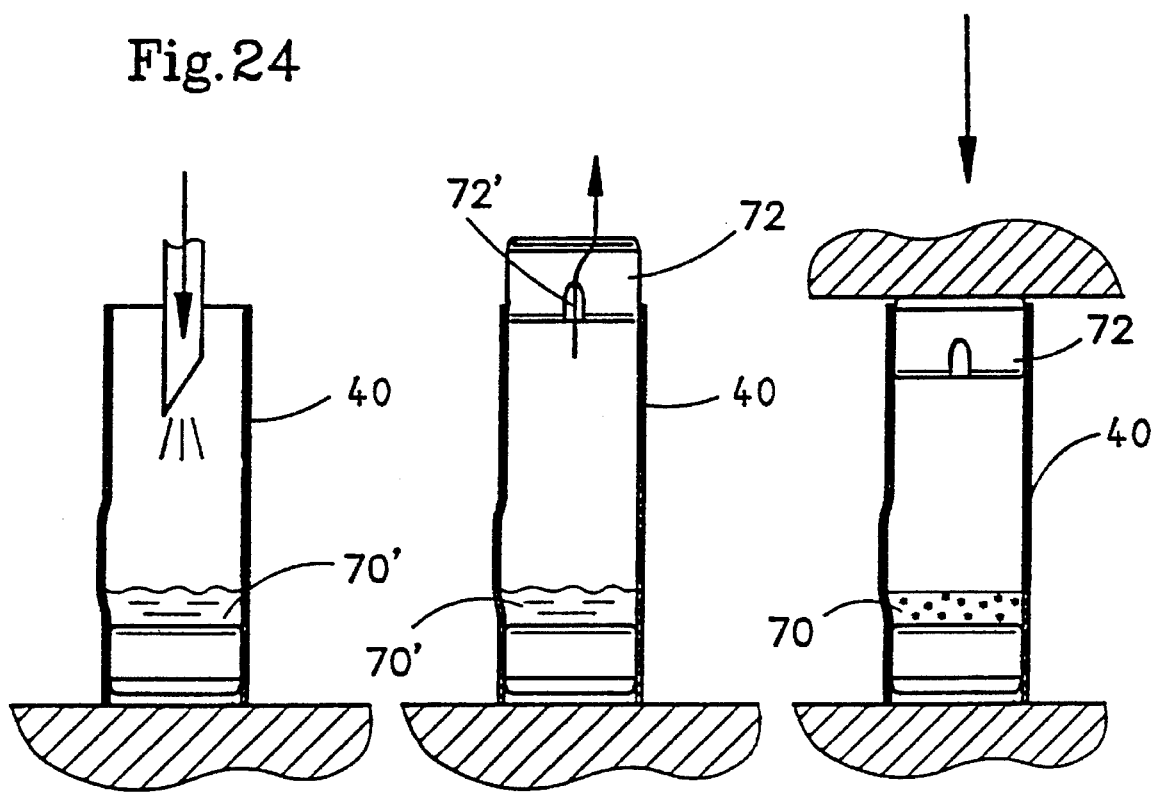

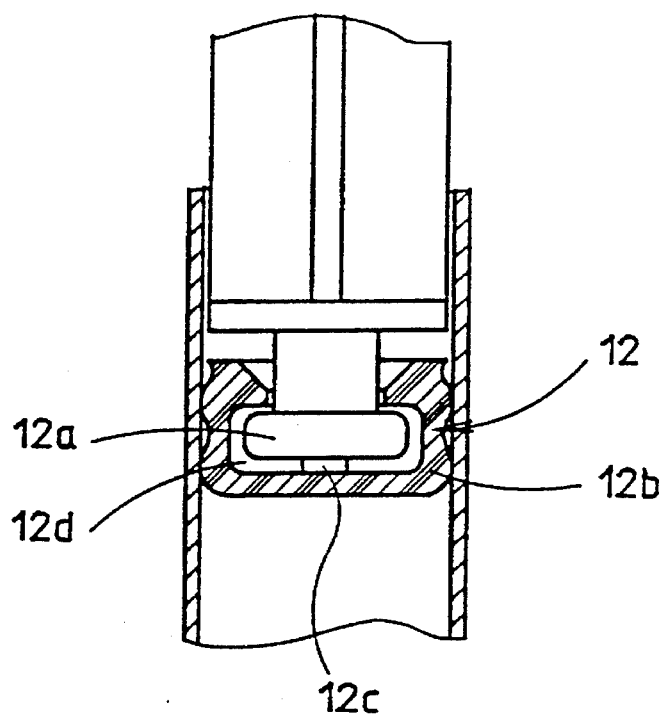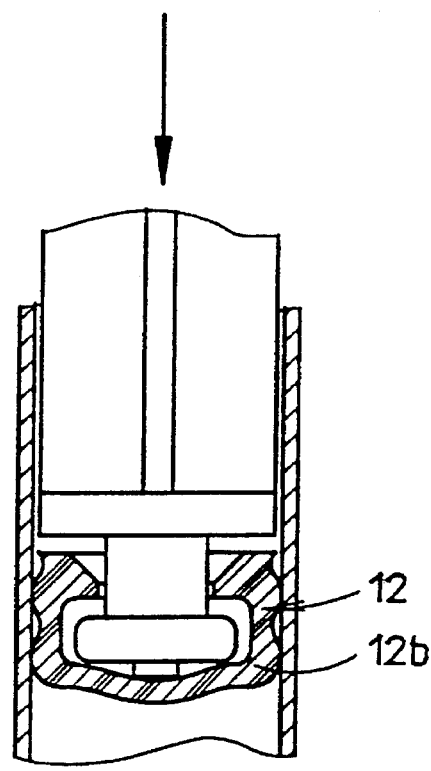
Fig.34  Fig.35
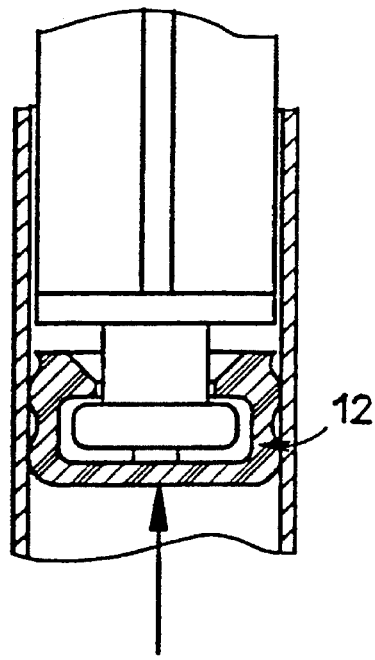
Fig.36

DEVICE FOR STORING A LIQUID MEDICINAL SUBSTANCE AND FOR ADMINISTERING EYE DROPS

This invention relates to a device for storing a liquid medicinal substance and for administering eye drops constituted by this substance, comprising a rigid cylindrical reservoir containing the said substance and a distributor fitted to one end of this reservoir, this distributor being provided with an applicator nozzle fitted with an orifice designed to form and deposit the said drops in the patient's eye.

Many such devices, which are all designed to store and to administer a medicinal substance intended to be deposited in the form of drops in the eyes of patients are already well-known. In most of such designs the reservoir comprises two walls made of a flexible synthetic material or is in the form of a bellows with folded walls to enable the user to apply pressure such as to cause the evacuation of the liquid in the form of the said drops.

When the said pressure is released, the elastic deformable reservoir creates suction in the applicator nozzle, which has the effect of sucking back inside the reservoir the last drop which had formed at the end of the said nozzle.

However, bacterial contamination of the applicator nozzle at the time of the administration of the drops is practically unavoidable given the proximity of this nozzle to the eye, the eye-lid or the eyelashes. The liquid which is in the immediate proximity of the end of the nozzle, and in particular the last drop which is formed there is necessarily particularly vulnerable to such contamination. In addition, the damp environment particularly favors the growth of germs, the migration of which inside the reservoir cannot be avoided. This migration is speeded up when the last drop is drawn back up into the nozzle.

In order to avoid the whole of the treatment substance contained in the reservoir becoming contaminated, and to prevent the bacterial contamination progressing, appropriate preservatives are added to this substance.

However, it should be noted that the bactericide effect of the preservatives is of limited duration. For this reason, the treatment solutions used as eye drops are only considered to be sterile for a period of approximately thirty days from the date of the first usage. This constraint leads to financial losses and gives rise to the risk of eye infections in patients who do not follow the instructions for use.

The known systems with a flexible reservoir made of synthetic material are not suited to traditional autoclave sterilization due to the high temperatures which the habitually used synthetic materials cannot withstand. This fact constitutes a second reason justifying the presence of bactericide preservatives.

Unfortunately, the presence of preservatives of sufficiently high concentration to be truly effective constitutes a considerable inconvenience as they give rise to major problems for the patient. They can cause denaturation of the cornea, irritations, allergies etc. . .

In order to eliminate the side effects resulting from such preservatives, the latter must be removed before the drops are deposited in the patient's eye.

A known method consists in equipping the device with a membrane, a pad or a filter which specifically absorbs the preservative at the moment when the drop is being administered. Such a method is, for example, described in U.S. Pat. No. 5,056,689. However, such absorbent methods are difficult to design so that they act specifically on the preservatives used without running the risk of acting upon the active substance of the treatment.

The possibilities of acting effectively are limited and their research and development would require major investment. The device of the U.S. patent is equipped with a unidirectional valve such as to try and avoid direct suction back via the distributor nozzle, and the said nozzle is fitted with another unidirectional valve to enable non sterile air to be admitted into the recipient. The presence of these two valves does not solve the problem of contamination of the nozzle and the solution. This design leads to extra costs, in addition to the cost of the absorbent material and the preservative itself. In practice, the preservative has been retained in this solution because of the back suction resulting from the elastic deformation which has proved unavoidable, and by the fact that no method enabling the proliferation of the germs in the nozzle applicator has been planned.

The same problems are created by the device described in the international application WO 91/16868. In addition, the device suggested has a number of disadvantages for the user, disadvantages which range from mere inconvenience of use to health risks.

Indeed, when the device comprising an elastically deformable recipient is fitted with a sterilizing filter which must without fail stay wet to be effective, an ever greater vacuum is gradually created inside the reservoir, given that the substance evacuated by pressure on the body of this reservoir is, after administration, partially drawn back in as far as the sterilizing filter, and prevents the penetration of air from outside. After use, the pressure on the flexible or folded walls of the reservoir, necessary to form the drops, becomes so great that this method becomes very unpleasant for the patient. Moreover, the phenomenon of back suction does not exclude all risks, because if the nozzle has been contaminated by the eye, such contamination can spread towards the inside of the device and possibly infect the sterilizing filter.

Another problem which is not solved with existing systems is that of the regularity and the precision of the drops formed.

It is known that an eye drop must have a volume of less than 30 microlitres to prevent the eye being "flooded". Moreover the optimum force which is to be applied by the user to enable him to generate an eye drop from a distributing device has been measured. This force is equivalent to approximately 300 grams and ought to be constant all the time the multidose device is being used. In addition, the device ought not to enable the formation of a jet whatever the force applied. Most known devices do not allow the formation of regular drops, nor the application of constant forces, this leads to a significant loss of substance and to disadvantages in use. Certain devices have tried to remedy these disadvantages by introducing a membrane which absorbs the preservatives but the solutions discovered are partial and are not totally satisfactory. The accurate formation of a drop without back suction or formation of an unwanted second drop cannot be guaranteed by the solutions offered, whether or not a preservative is present.

It has been noted that to protect the patient's health all preservative must without fail be removed, and that the methods used to absorb preservatives have not succeeded in solving the problems of contamination of the nozzle, nor of distributing drops with a constant force and with any precision, and in a way that is not unpleasant. To this must be added the fact that due to the back suction, some solutions do not remain homogeneous and form a foam, which results in unacceptable variations in the dosage.

The specifications of a device enabling the complete elimination of any preservative in the solution and in the drops whilst at the same time guaranteeing the continued sterility of the solution contained in the recipient, and that remaining in the channels of the distributing implement, render preferable the presence of the following methods:

a method enabling the evacuation of the solution with constant force;

a method making it possible to avoid the creation of a vacuum within the recipient;

a method making it possible to control the flow rate with forming a jet;

a method making it possible to remove residual pressure from inside the recipient after accurate administration of a drop to avoid the formation of a second drop outside the nozzle;

a method making it possible to provide a tight and secure seal with no risk of error, without causing excess pressure, or a return of the solution contained in the nozzle;

a method making it possible to prevent turbulence and air/solution mixes inside the distributor nozzle such as to form homogeneous drops without forming any foam;

a method making it possible to prevent the migration of germs inside the recipient; and a method making it possible to prevent the proliferation of germs inside the distributor nozzle.

Some of these methods could be provided by injection syringes such as the one described for example in the publications GB-A-2 010 681 and EP-A-O 207 544, but the solutions offered are only partial and are not satisfactory at all levels and thus have no chance of being accepted as a preservative-free ophthalmic device, as only the presence and the control of the above methods make it possible to guarantee the distribution of sterile drops.

Indeed, injection syringes fitted with drop-counter nozzles and sterilizing filters could form, in an imprecise and uncontrolled manner, drops whose sterility could not be guaranteed given the absence of most of the methods mentioned above.

Whereas in a syringe the "back suction" function is indispensable for filling it up and for testing the presence of blood, this function is absolutely prohibited in eye drop applicators where it is necessary to maintain sterility within the bottle, when the latter is of the multidose type.

A device which distributes eye drops is necessarily of the multidose type, whereas a syringe is necessarily of the monodose type to preserve sterility.

Finally, there are sterilizing membrane filters which can be connected to injection syringes. Such filters can also act as flow rate controlling devices and aseptic back-flow barriers to prevent contamination of the contents of the syringe. By modifying the connection between the syringe piston and its plunger in order to prevent back suction, the disadvantages of which have been mentioned above, it would be possible, with the device thus obtained, to distribute drops one by one without forming a jet and without risking contamination of the inside. Despite this major modification of the essential functions of a syringe which ought also be fitted with a drop distribution nozzle, it would not be possible to distribute drops accurately given the residual pressure, nor to eliminate the risk of contamination and bacterial growth downstream from the filter between two applications. This observation is applies also to all previous devices, even those fitted with devices enabling the absorption of preservatives contained in the medicinal substance, as contamination of the nozzle is inevitable and the risk of bacterial growth downstream from the preservative absorption devices is unavoidable.

Moreover, the uncontrolled residual pressure gives rise to undesirable flows as soon as pressure is removed from the piston, whereas the flow should cease immediately to separate the drop precisely. This cannot be achieved with a traditional piston.

The present invention is intended to overcome the above-mentioned disadvantages and offers a device which satisfies the requirements stipulated in the above specifications and the most recent requirements, whilst at the same time simplifying manufacture and facilitate use by the patient.

In this aim, the device according to the invention is characterized by the fact that the reservoir is sealed at the end on which the distributor is fitted by a flow rate control device comprising a regulator element the opening of which is dependent upon a threshold pressure applied to the said medicinal liquid substance, and by the fact that this reservoir is sealed at its other end by a sliding piston engaged in the said reservoir, the said piston being arranged such as to generate the said threshold pressure, and in that the flow rate controlling device is connected to asepticization devices having an oligodynamic action on a predetermined volume of medicinal substance situated upstream from the said orifice.

Depending on the forms of realization, the flow rate control device can comprise at least one membrane with calibrated micropores, at least one calibrated orifice or at least one narrow channel.

Preferably, the reservoir comprises in addition an additional movable sealing method arranged to prevent contact of the medicinal substance with the flow rate control device during storage of such substance.

This additional movable method of sealing can be a movable sealing plug and the reservoir can comprise a bypass chamber to accept, at least partially, this plug when the medicinal substance is being used.

In one advantageous form of realization, the movable sealing plug comprises at least one ring-shaped bead to ensure impenetrability of the reservoir during storage and at least one lateral recess to ensure the flow of the medicinal substance during use, this recess being arranged to communicate with at least one recess made in the base of the reservoir.

Depending on the form of the realization the height of the bypass chamber can be less than or greater than the height of the movable sealing plug.

Preferably, the movable sealing plug comprises a central area of reduced thickness and the reservoir is fitted with a needle arranged to pierce the central area of this plug.

Advantageously the said needle is fixed and mounted close to the flow rate control device.

The said needle can also be mobile and mounted on a mobile needle carrier support.

In another form of realization the movable sealing plug comprises a unidirectional valve.

To reduce as much as possible the residual volume of the reservoir, the movable sealing plug and the mobile piston can comprise respectively at least one recess and one protuberance of complementary form and dimensions.

In all variants, the flow rate control device is arranged on the base of the distributor, and preferably in the base of the applicator nozzle of this distributor.

In an advantageous form of realization, the device contains at least one vent arranged at the end of the reservoir and leading into the bypass chamber to enable the evacuation of gases contained in this chamber before using this device.

The reservoir may contain two compartments separated by a mobile intermediate plug, one of the compartments containing a solvent and the other compartment containing a substance designed to be dissolved or mixed with the solvent.

In this form of realization, the reservoir comprises advantageously a central enlargement arranged to enable the passage of liquid solvent, when the intermediate mobile plug is brought into the vicinity of this enlargement.

In an advantageous form of realization the device comprises a hood limiting the stroke of the plunger in order to ensure the components are mixed.

In order to eliminate residual evacuation of the liquid after use, the piston may comprise a rigid retention stop and a flexible lining defining an internal cavity, this retention stop comprising a supporting stud and the total height of the said stop with the supporting stud being roughly equal, at rest, to the height of the internal cavity.

In the preferred form of realization of the device the piston comprises a spiral ring arranged such as to apply a gradual thrust.

Advantageously, in all forms of realization, the reservoir comprises a cylindrical jacket which constitutes its side walls.

In a particularly economical and efficient form of realization, the cylindrical reservoir is made up of a first tubular element and a second tubular element which fit one inside the other, the first being sealed by a fixed seal and by a mobile piston and the second containing a hollow rigid element mechanically linking the mobile piston and the sliding piston, the said fixed seal comprising a unidirectional valve allowing the flow of the medicinal substance towards the distributor, and the bottom of the said second tubular element being closed.

The said cylindrical reservoir is advantageously sealed by a sliding piston which is solidly linked to a hollow rigid element mounted at the bottom of a capsule in which the said cylindrical reservoir is partially inserted, and the said hollow element communicates with the distributor via a filter and/or the said asepticizing devices.

In accordance with an advantageous method of realization, the said flow rate controlling device contains a depth filter.

This depth filter may be comprised of a sintered material containing at least one element having an antibacterial oligodynamic effect, chosen from among heavy metals, compounds or mixtures of these metals and mixtures of these compounds.

The said asepticizing devices contain silver and/or silver oxide.

In accordance with a preferred method of realization, the device is arranged such that the said predetermined volume is less than the volume of a drop and, advantageously, the ratio between the predetermined volume measured in microlitres and the surface area of the said asepticizing devices in square millimetres is less than 1.

In order to avoid residual evacuation after use, the piston is, preferably, provided with elastic devices arranged to absorb residual pressure.

The said elastic devices contain advantageously a less resistant area installed on the piston side in contact with the medicinal substance and arranged to change shape under the thrust exerted on this piston and to return to its normal state at the end of this thrust.

The present invention will be better understood by referring to the description of an example of the realization and the drawing annexed hereto in which:

FIG. 1A and 1B represent an axial cross section of a form of realization preferred for the device in accordance with the invention.

Figure 2:
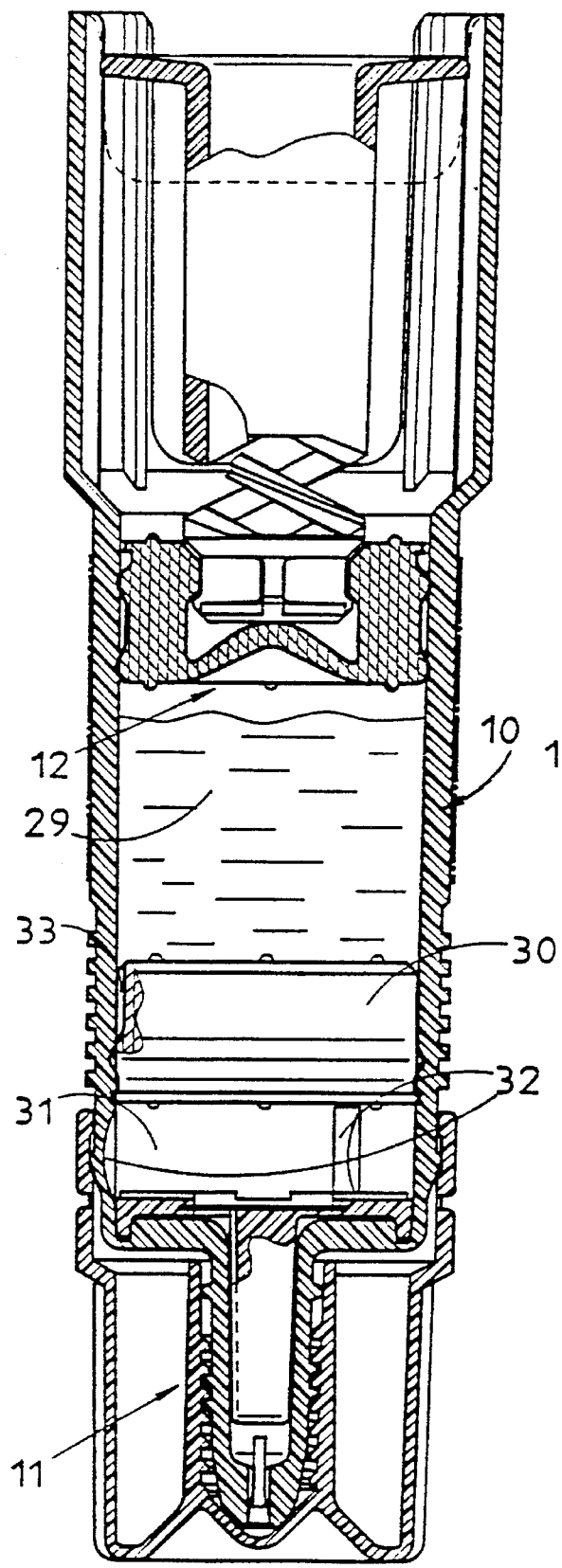
Figure 3:
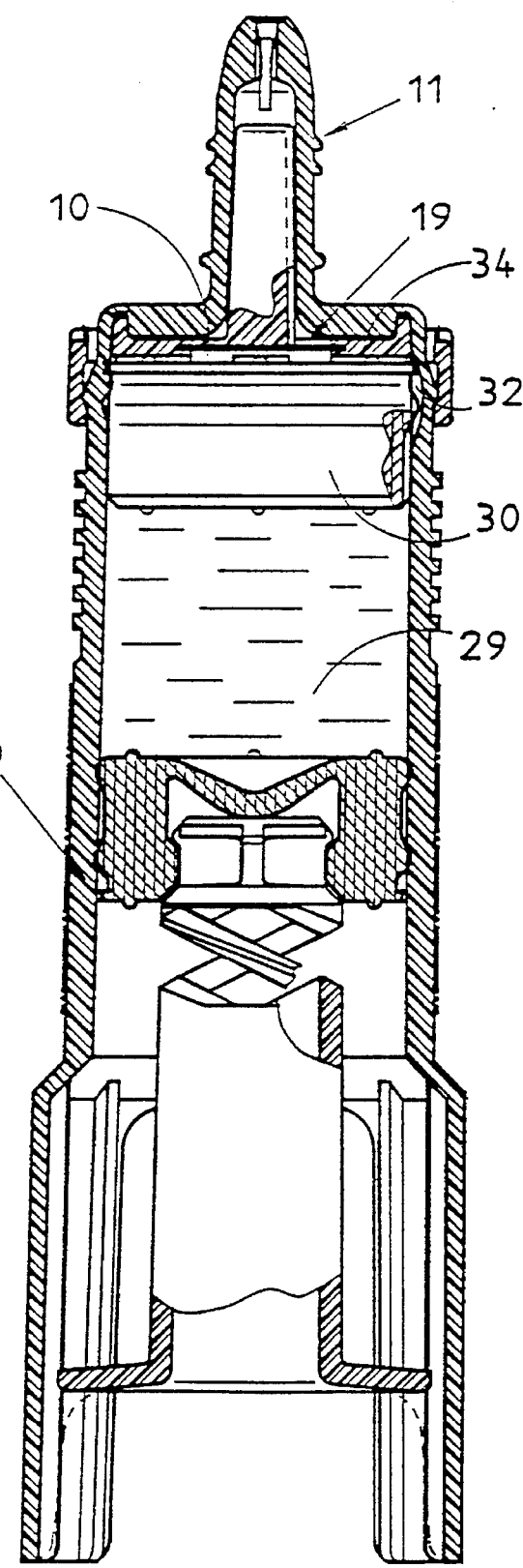
Figure 4:
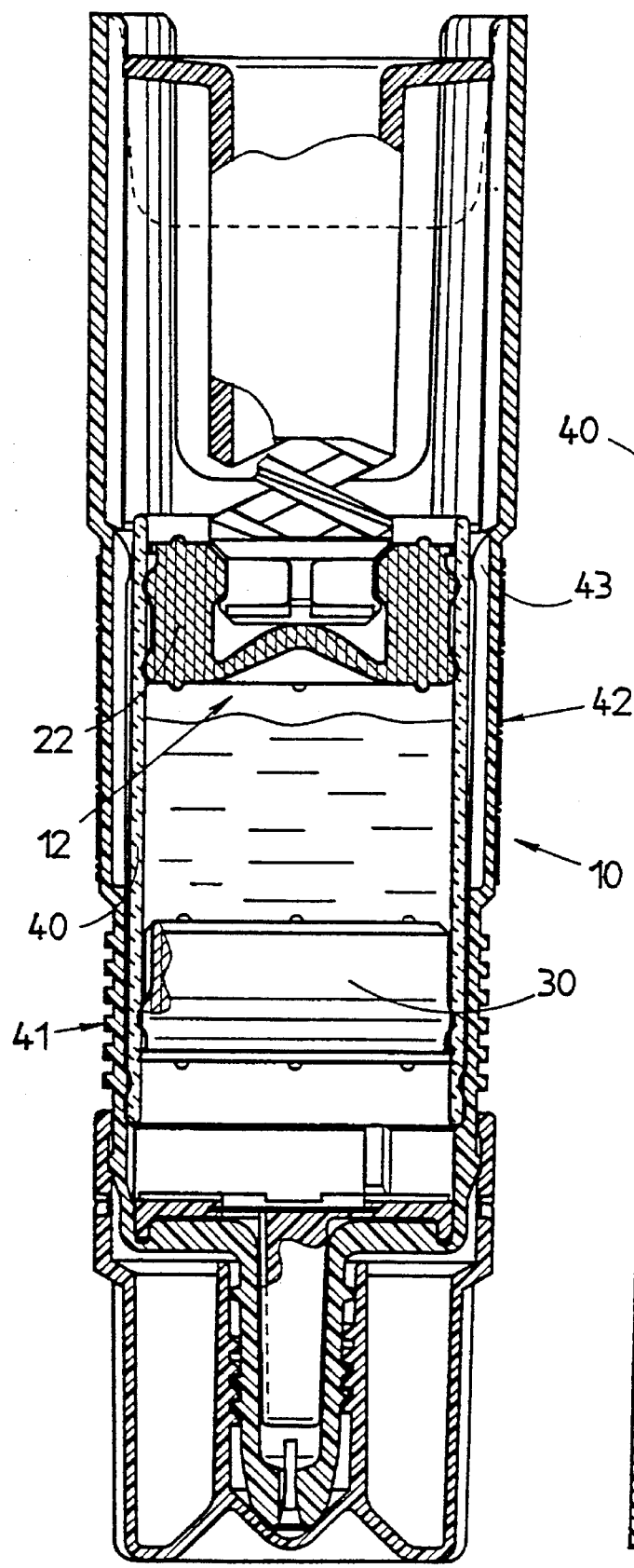
Figure 5:
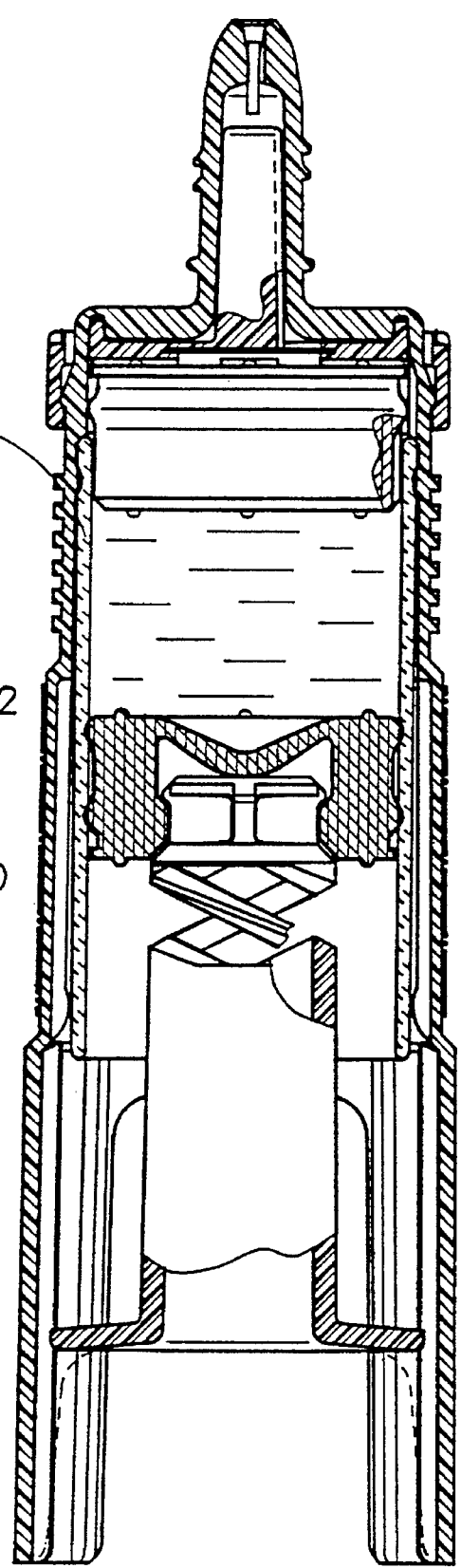
Figure 6:
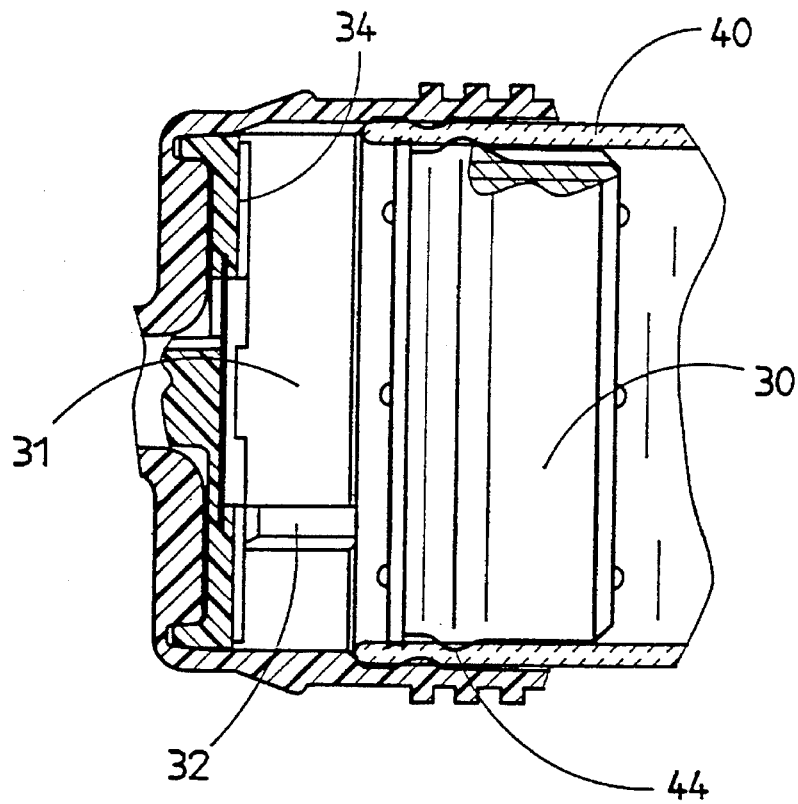
Figure 7:
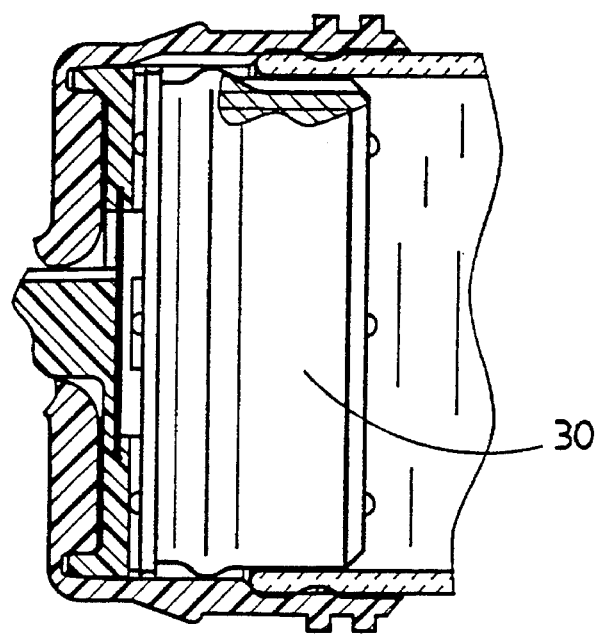
Figure 8:
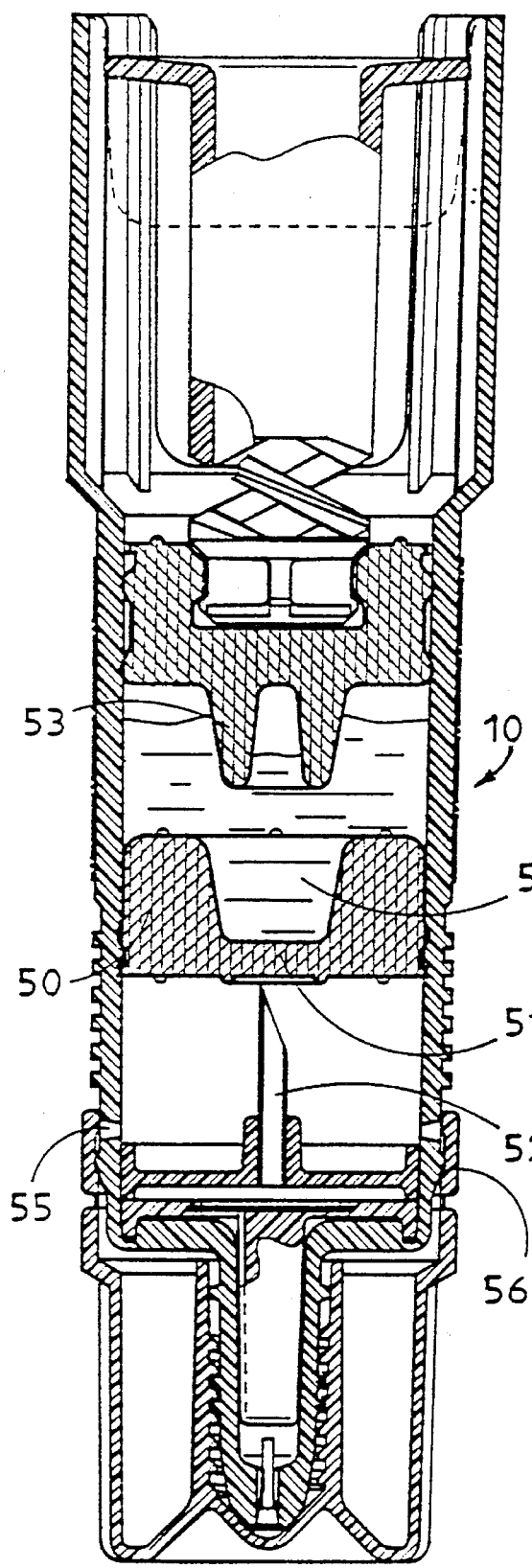
Figure 9:
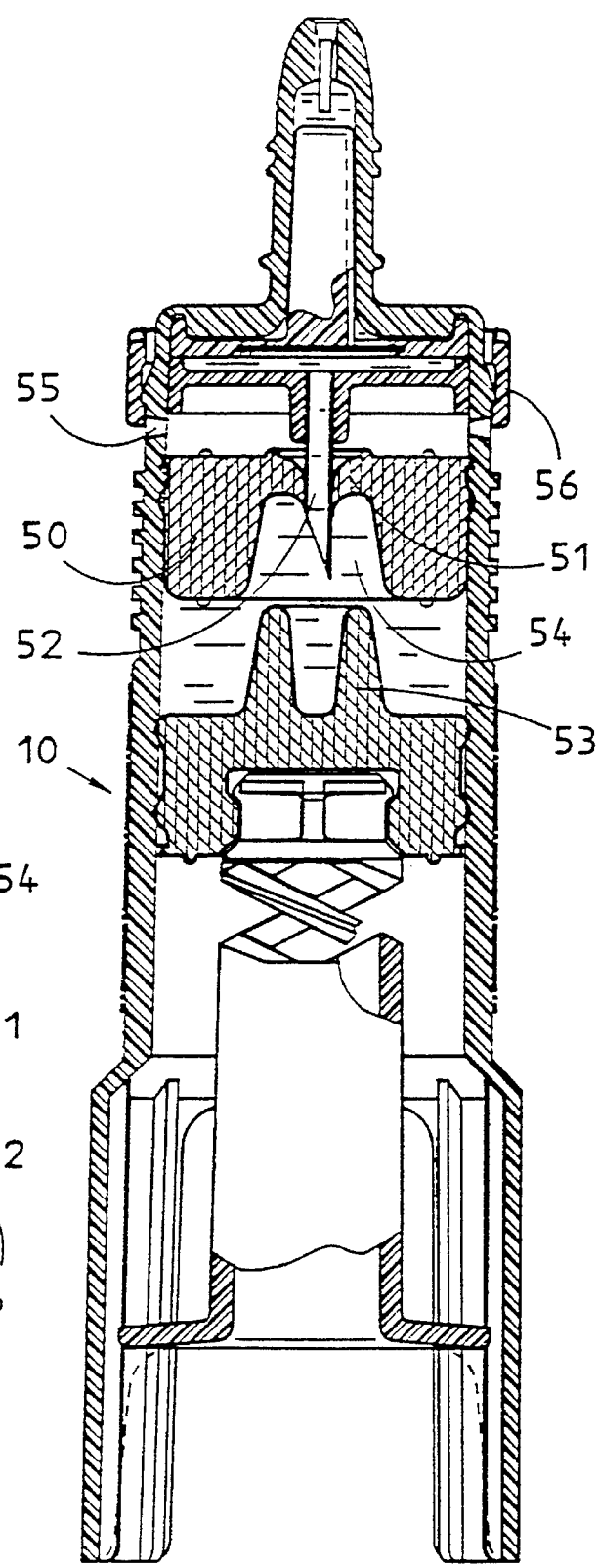
Figure 10:
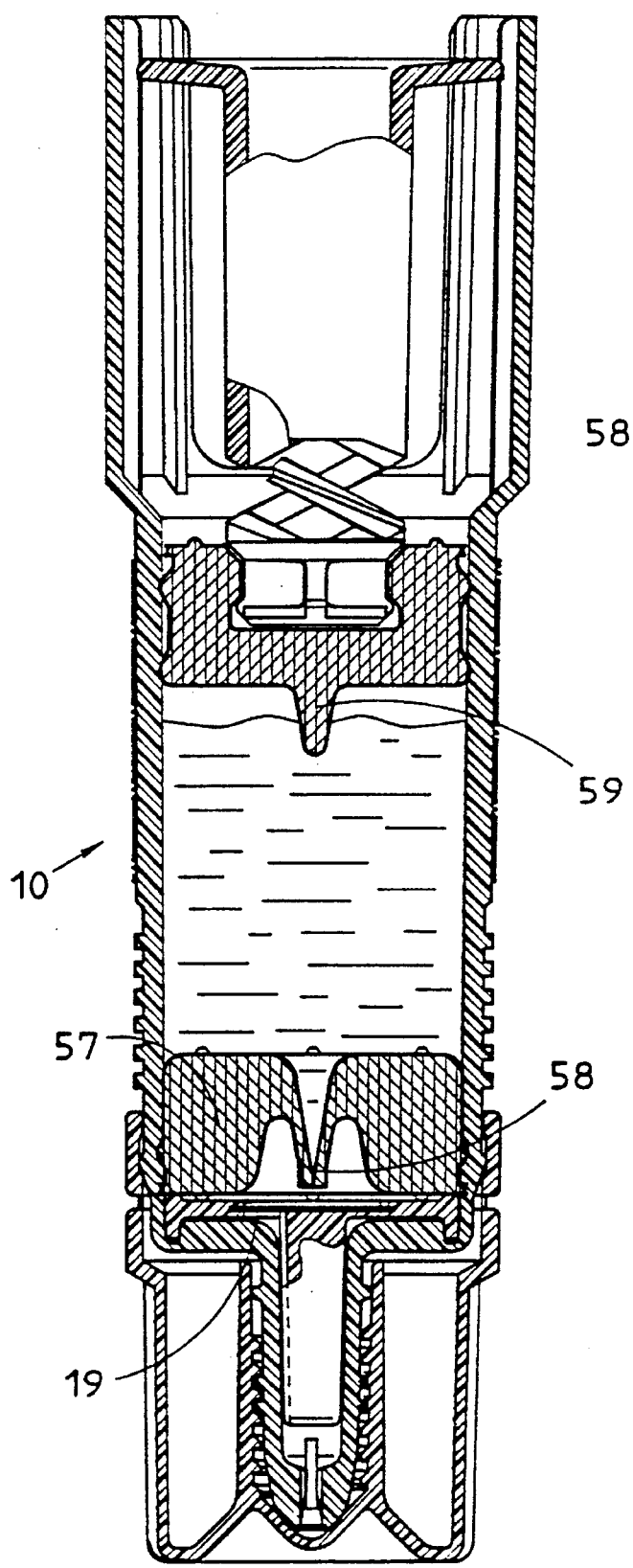
Figure 11:
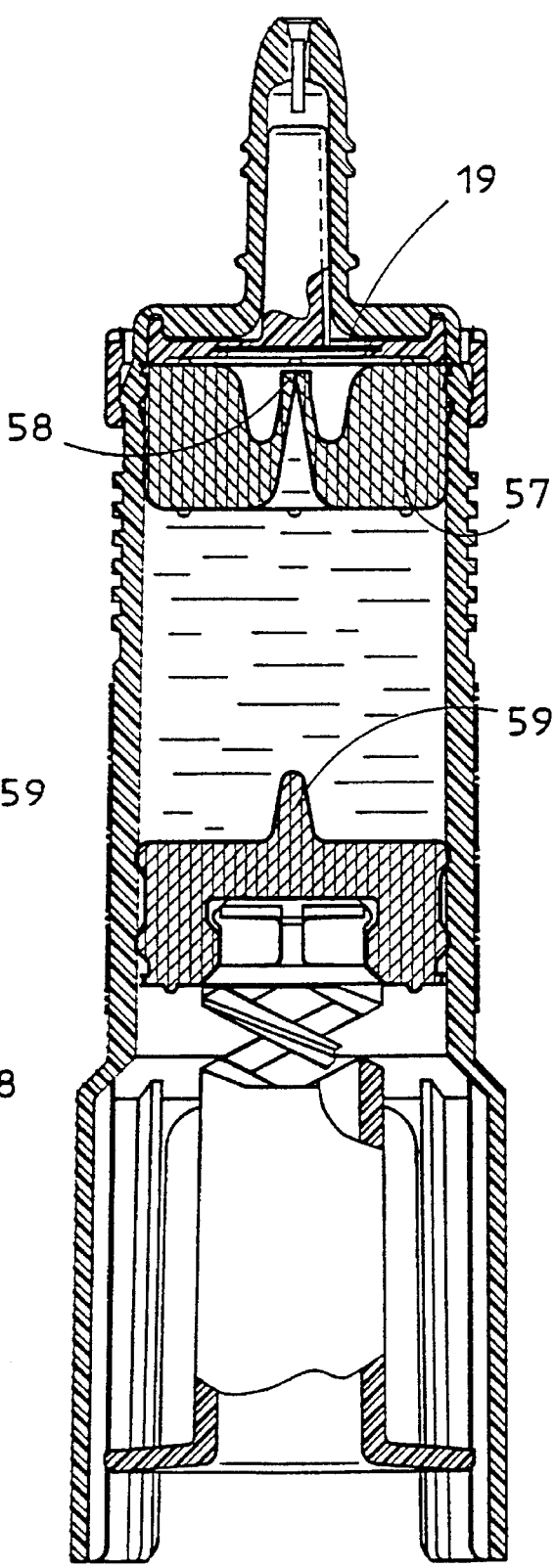
Figures 21, 22, 23:
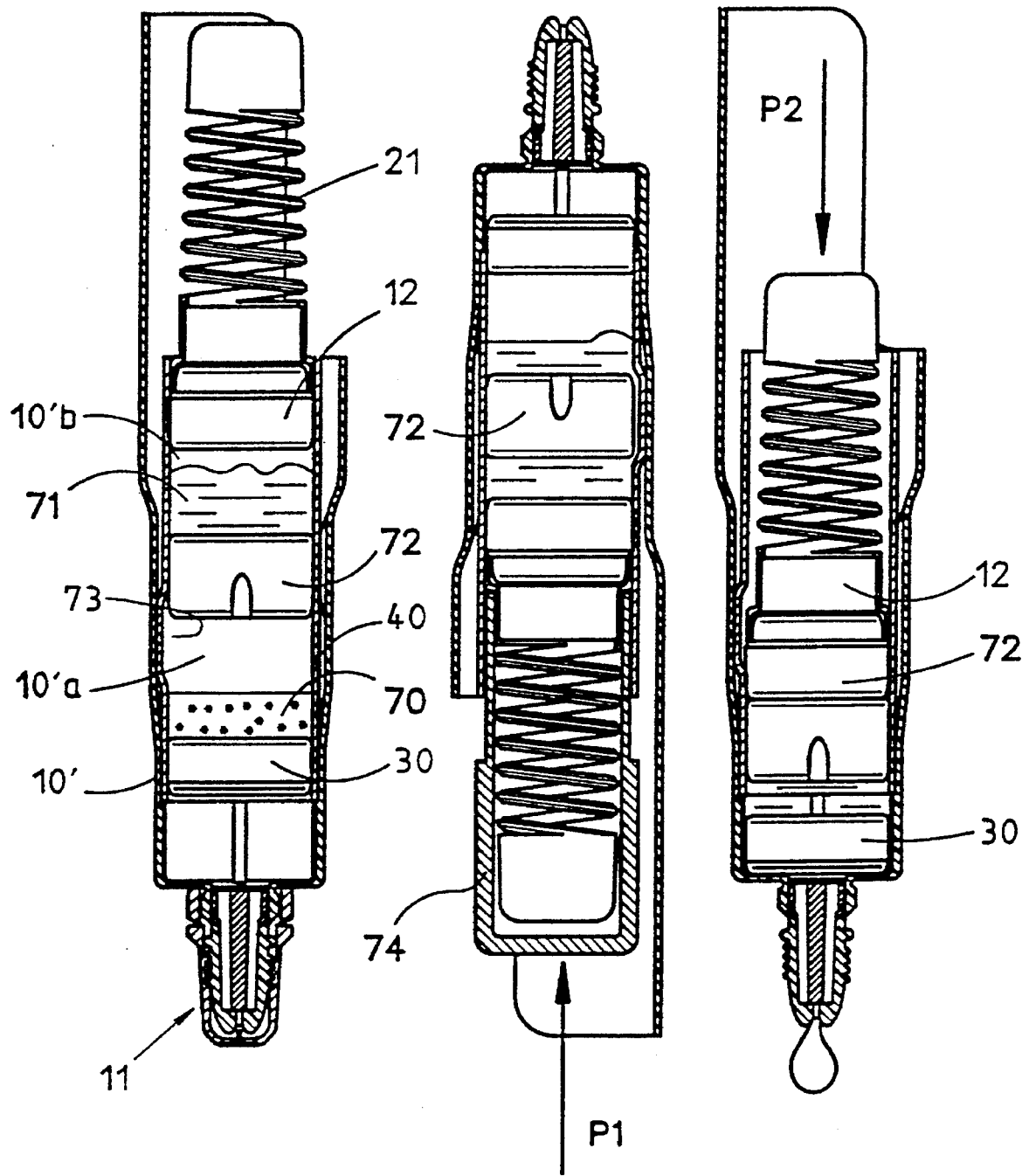
Figure 37:
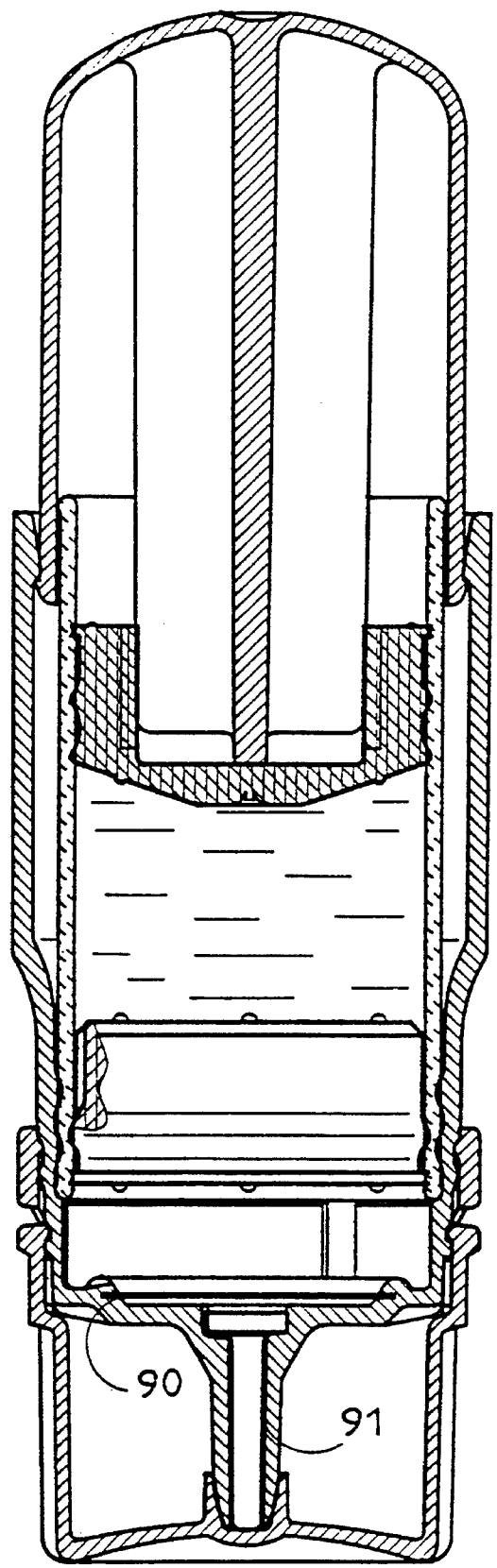
Figure 38:
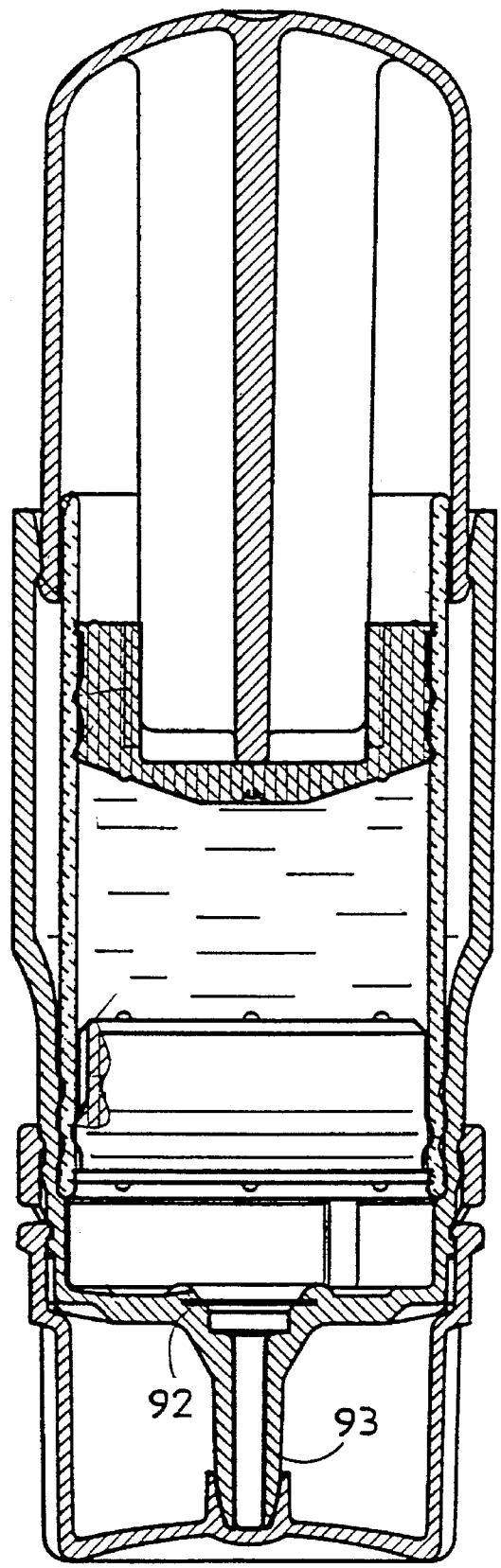
Figure 39:
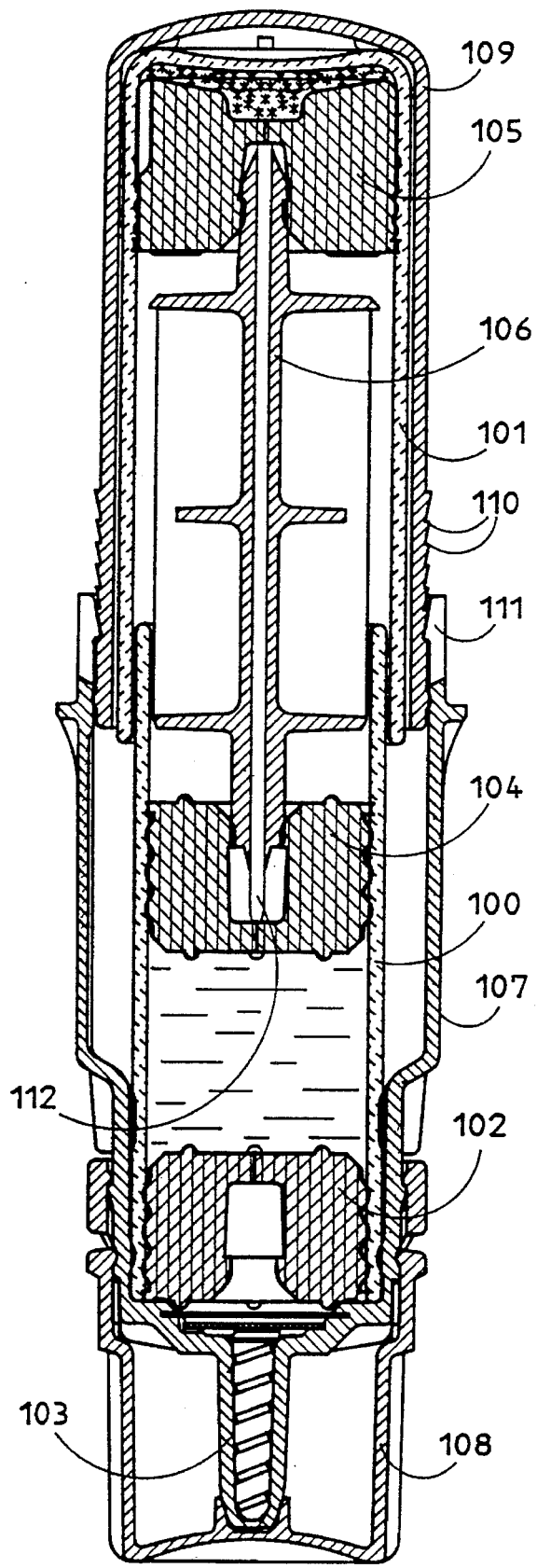
Figure 42:
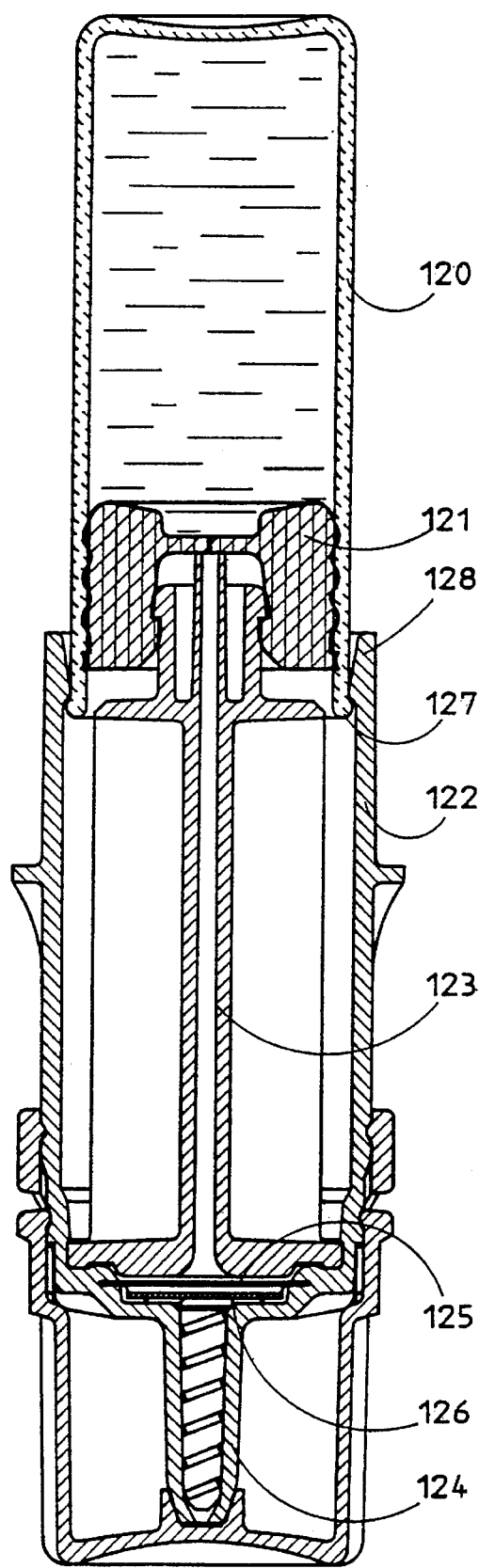
Figures 40, 41:
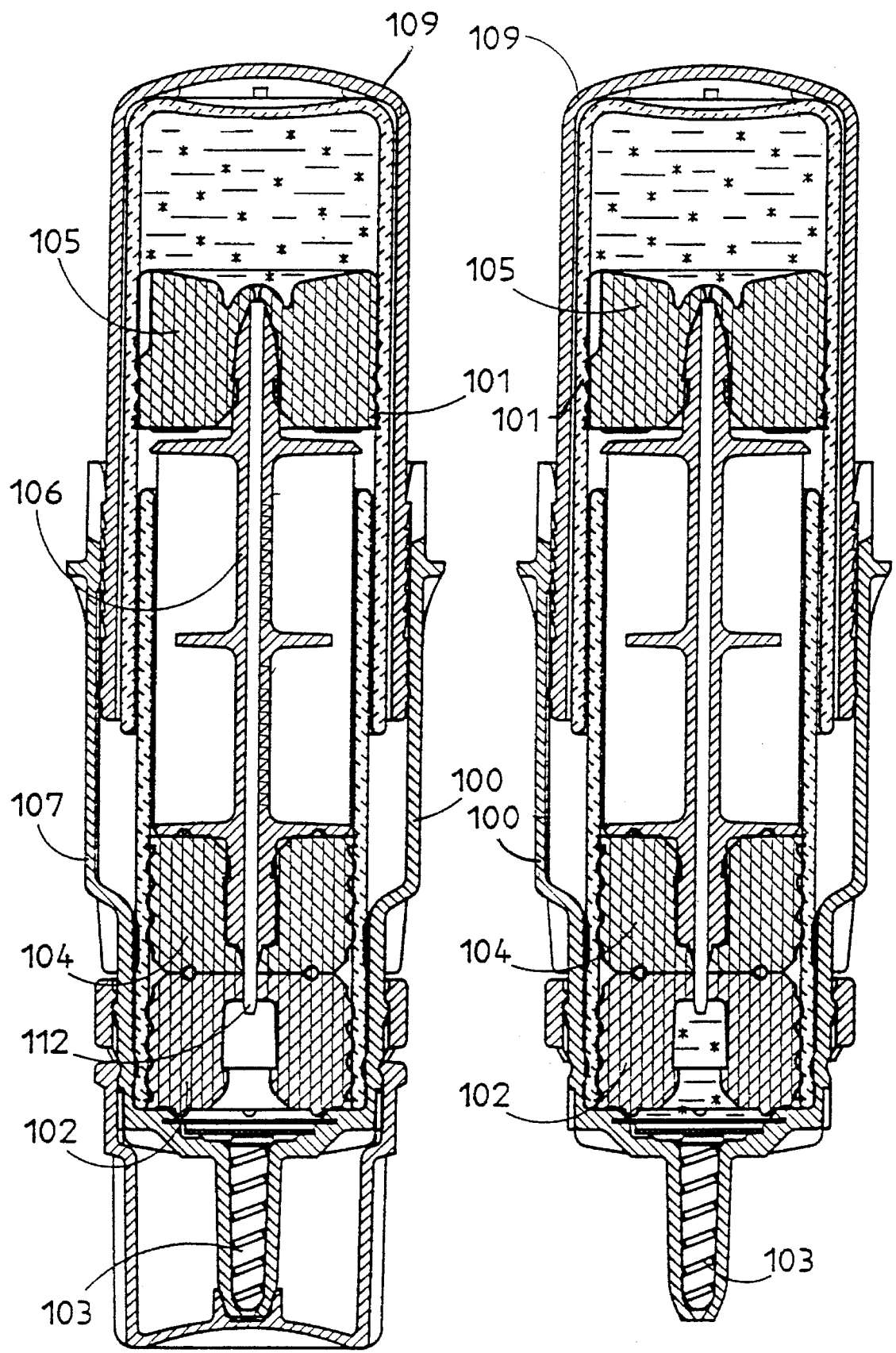
Figure 43:
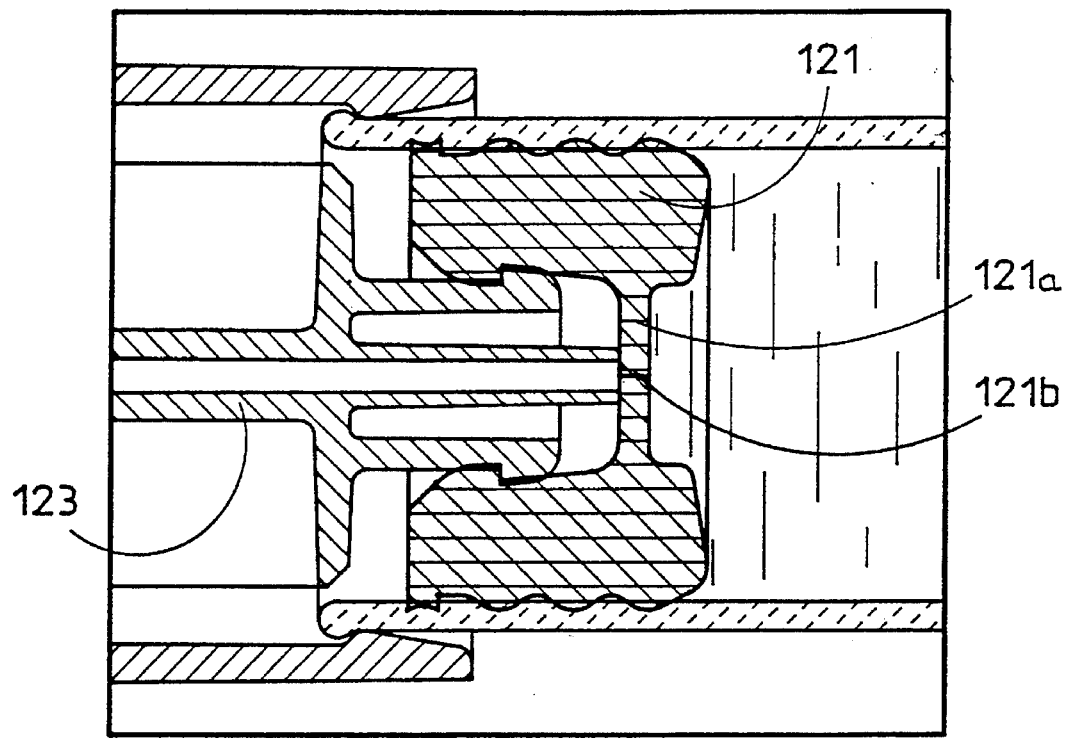
Figure 44:
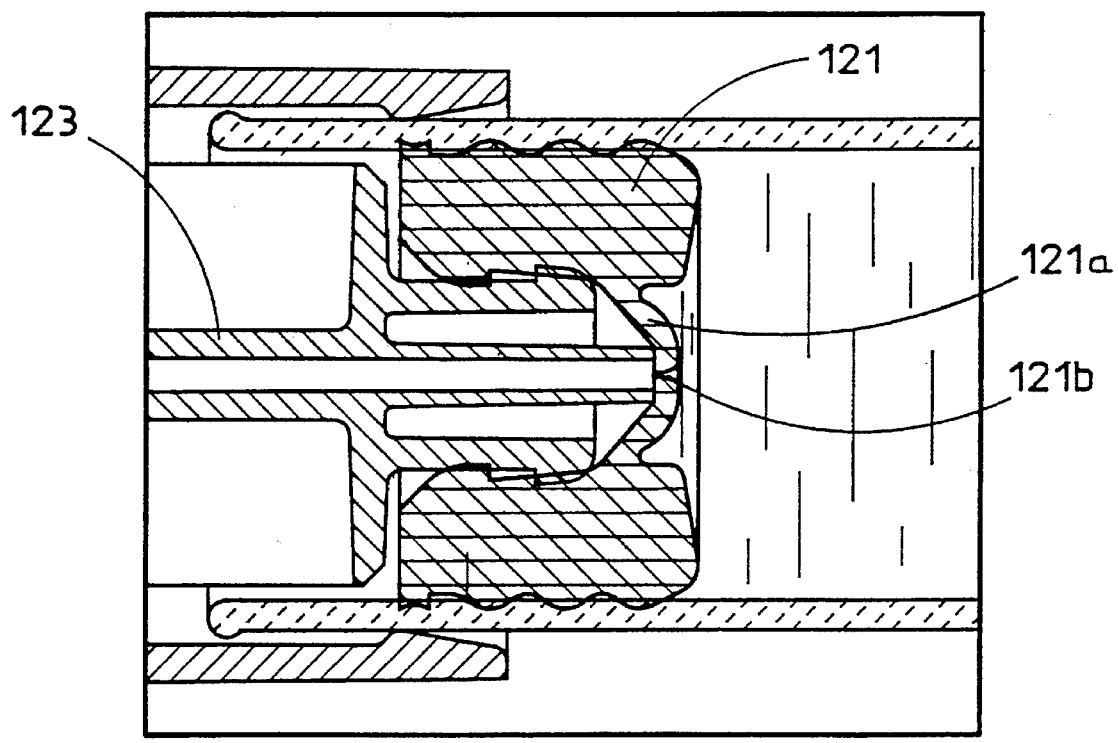

FIGS. 2 and 3 represent another form of realization of the device in accordance with the invention, respectively in the storage position and in the position when used, FIGS. 4 and 5 represent a variant of the device in accordance with the invention, respectively in the storage position and in the position when used, FIGS. 6 and 7 represent detailed views of the device in accordance with the invention, FIGS. 8 and 9 represent another variant of the device in accordance with the invention, respectively in the storage position and in the position when used, FIGS. 10 and 11 represent another variant of the device in accordance with the invention, respectively in the storage position and in the position when used, FIGS. 12 to 20 illustrate the various phases of preparation of the elements and the assembly of these elements to obtain the devices in accordance with the invention ready for storage, FIG. 21 represents a special form of realization of the device in accordance with the invention, the reservoir of which comprises two compartments, this device being represented in its storage position, FIG. 22 represents the device of FIG. 21 in an intermediary position, FIG. 23 represents the device in accordance with the invention in the position when used, FIGS. 24 to 33 illustrate the different phases of preparation of the elements and of the assembly of these elements to obtain a device the reservoir of which contains two components, such as represented by FIGS. 21 to 23, FIGS. 34 to 36 illustrate a preferred form of realization of the piston respectively at rest and during use, FIGS. 37 and 38 represent two views illustrating two forms of realization of the device of the invention in its storage state, FIG. 39 represents a cross section view of a particularly advantageous form of the device of the invention, in its storage phase, FIGS. 40 and 41 represent the realization of FIG. 39, respectively in the activation and the distribution phases, FIG. 42 represents a variant of the realization of that illustrated by FIG. 39 and FIGS. 43 and 44 represent detailed views illustrating the sliding piston of the device in accordance with FIG. 42, respectively during storage and during use.

By reference to FIGS. 1A and 1B, the device represented in its preferred form comprises essentially a cylindrical reservoir 10, a distributor 11 fitted to one end of this reservoir and a sliding piston 12 engaged in this reservoir at the end opposite the distributor. A protective hood 13 is mounted over distributor 11.

This distributor is made up of an applicator nozzle 14 having an orifice 15 which is designed to enable the formation of eye drops designed to be deposited in the patient's eye. This orifice communicates with a chamber 16 made in the end of the applicator nozzle, which is itself connected with the inside of the reservoir via a side channel 17 made between the inside wall of the applicator nozzle and an insert 18, and via a flow rate control device 19 which shall be described below.

This flow rate control device is comprised in this case of a calibrated micropore membrane or filter which seals one end of the reservoir, the other end being sealed by the piston 12.

This piston is mounted on the end of a piston rod 20 or plunger via a spring element 21 the role of which will be explained subsequently.

The piston 12 is in fact made up of a sealing plug 22 in the form of a ring-shaped skirt made in an elastomer material, which is fixed on the edge of a rigid stop 23 connected via the spring element 21 to the plunger 20.

In the form of realization represented, the orifice 15 is made up of the end of an axial channel which crosses the upper part of the applicator nozzle. In this channel, preferably, a silver tip 24 is lodged which has bacteriostatic effects through the release of cations, and which maintains the said orifice of the applicator nozzle in an aseptic state. As FIG. 1B more specifically shows, this silver rod 24 is maintained in an axial position centered by at least two radial blades 25. It could be replaced by any equivalent material having the same functions or even by a coating of the same nature covering the inside wall of this channel near the orifice 15.

When the protective hood 13 is placed on the device, i.e. when it is screwed on the applicator nozzle fitted with a male thread 26, the hood itself being fitted with a corresponding female thread 27, the end of the channel which constitutes in fact the tip of the applicator nozzle defines a microchamber 28 close to the orifice 15 in which part of the medicinal substance 29 contained in the reservoir 10 may remain, after initial use. This quantity of treatment substance is asepticized via the silver tip with which it comes momentarily or remains in contact.

The flow rate control device 19 is made up of one or more membrane filters comprising calibrated micropores, which makes it possible to accurately control the flow rate of the medicinal substance flowing through the side channel towards the orifice 15 of the applicator nozzle. This device makes it possible to bring about a loss of load, when crossing through the treatment substance, which is proportional to the pressure exerted on the solution by the piston 12. Given that the section of the cylinder is relatively high, for example in the order of 250 mm2, it would be necessary to apply a thrust in the order of 2.5 kg. to achieve a pressure in the order of 1 bar in the solution. However, it is accepted that in practice a force of 1 kg. is already considered to be high to activate the system, i.e. push the piston in with the index finger. The maximum pressure is situated approximately at 0.4 bar and tests show that even by exerting a force equivalent to 2 kg., it is not possible to form a jet at the end of the applicator nozzle, but unit drops in accordance with the design. Experience has shown that as a result of the flow rate control device, drops are formed every one or two seconds outside the orifice 15. These drops have a volume of between 20 and 40 @1.

The spring element 21, which cannot be considered indispensable, but which contributes to the ease of use of the device, makes it possible in fact to gradually transmit the thrust exerted by the user on the piston rod or plunger. It complements, in a manner of speaking, the function of the flow rate control device by preventing the application of a sudden excessive thrust on the substance 29 contained in the reservoir 10.

FIGS. 2 and 3 illustrate a form of realization in which reservoir 10 is elongated and sealed, close to its distal end, i.e. in the vicinity of the distributor 11, by a movable sealing plug 30, which is designed to be pushed back at least partially in a bypass chamber 31 at the moment when the user pushes in the piston 12 by pressing the plunger 20.

The bypass chamber 31 comprises side recesses 32 which enable the medicinal substance contained in the reservoir 10 to flow out by one or more axial channels 33 made between the movable sealing plug 30 and the inside wall of the reservoir, these channels communicating with the recesses 32 which themselves communicate with one or more radial ducts 34 which lead onto a central area 35 located upstream of the flow rate control device 19 constituted by a membrane filter.

This realization is designed for cases when the medicinal substance contained in the reservoir cannot withstand long-term contact, which may be as long as three years, with the flow rate control device i.e. with the membrane filter, whereas this contact is quite possible for a duration of use in the order of one month. The movable sealing plug has the sole task of retaining the medicinal substance 29 within a closed space formed by the walls of the reservoir 10, the ring-shaped skirt of the sealing plug 22 and the said movable sealing plug 30.

FIGS. 4 and 5 illustrate this form of realization which is different from the preceding form in that the reservoir is lined or, in other words, comprises a glass cylindrical jacket 40 which covers the inside walls of the reservoir. In this realization, the medicinal substance is enclosed in a space formed by the glass jacket 40, the movable sealing plug 30 and the sealing plug 22 of the piston 12.

In order to facilitate the installation of this independent reservoir defined by the three above components inside the body of the reservoir 10, the walls of the reservoir advantageously have a first area 41 the interior surface of which is smooth and which has roughly the same diameter as the external diameter of the jacket 40, and a second area 42 the internal diameter of which is a great deal larger than that of the jacket 40. As a result the jacket 40 which will only be held in place by the friction against the inside wall of the first area 41, and possibly by centering tongues 43 made in the second area 42, may be easily placed in position, without the need for excessive thrust.

In this realization it will be possible to achieve fully automatic filling of the independent reservoir, as will be explained with reference to FIGS. 12 to 17, this reservoir being introduced into the body of the device with a view to storing and then to making use of the latter.

FIGS. 6 and 7 are enlarged views which show in greater detail the form of realization and the operating method of the movable sealing plug 30 in the device illustrated by FIGS. 4 and 5. This sealing plug presents at least one ring-shaped bead 44 which is partially squashed when this sealing plug is in its storage position, i.e. engaged inside the jacket 40 of the reservoir 10 and which enables the passage of the medicinal substance when in use. As a result of the recesses 32 similar to those defined with reference to FIG. 2, and to the position of bead 44, the height of the bypass chamber 31 is less than the height of the movable sealing plug, which makes it possible to reduce the overall length of the body of the reservoir 10, relative to realizations in which the bypass chamber must be sufficiently high to accept completely the said movable sealing plug.

The design illustrated by FIGS. 8 and 9 is different to the preceding realization in that the movable sealing plug is replaced by a sealing plug 50 which is designed to be pierced. To this end, this sealing plug comprises a thinner central area 51 and a needle 52 is mounted at the bottom of the reservoir opposite the applicator nozzle. The ring-shaped skirt of the piston has two protuberances 53 having a form roughly complementary to that of the recess 54 of the movable sealing plug in the thinner central area 51.

Lateral orifices 55 serving as vents, sealed during the storage phase by the protective hood 15, enable the evacuation of gases initially contained inside the reservoir downstream from the movable sealing plug 50 when this plug is moved and when the hood is unscrewed. In fact these openings 55 are sealed by a lower part of the protective hood, this lower part constituting a tamper-proof ring 56 attached to the rest of the hood by linking arms which break in order to free these orifices when the user wishes to make use of the device.

It would also be feasible to modify this design by mounting the needle 52 on a mobile needle carrier support which could be pushed into the inside of the reservoir to ensure the perforation of the sealing plug.

FIGS. 10 and 11 illustrate anther form of realization, derived from that of the FIGS. 8 and 9, in which the movable sealing plug 57 is fitted, in its central area, with a unidirectional valve 58 constituted by a narrow aperture which, in the absence of any pressure exerted on the medicinal substance 29, is closed and only opens to let through this substance towards the flow rate control device 19, when the pressure is sufficient to open the lips of this unidirectional valve.

The ring shaped skirt of the piston presents in this case a protuberance 59 the shape of which is preferably complementary to that of the recess made between the lips of the unidirectional valve such that, after use, this protuberance penetrates into this recess to reduce to a minimum the dead volume or residual volume of the reservoir.

In all preceding realizations, the flow rate control device has been represented in the form of a membrane filter comprising a predetermined number of calibrated micropores. It should be noted that this type of flow rate control device could be replaced by any other appropriate means such as, for example, a sufficiently small calibrated orifice, a straight or spiral narrow channel or any other appropriate means making it possible to moderate the flow rate in order to avoid the formation of a jet and to encourage regular drops, whatever the pressure exerted on the piston.

The membrane filter is advantageously a sterilizing filter the pores of which may have a diameter between 0.1 and 0.45 microns preferably in the region of 0.22 microns such as to stop all solid particles, as well as bacteria or other foreign bodies the dimensions of which are greater than these values.

In all these realizations, at least one filter is planned which has the main function of controlling the flow rate, and at the same time a function of being an anti-particle, antiseptic filter absorbing the preservatives. The device may comprise a second element such as for example a membrane filter or a pad to absorb the preservatives.

Advantages in use result directly from the designs described above. Among the advantages directly perceptible by the user, that of the regularity of the accuracy of the drops, which are formed on the end of the applicator nozzle when the plunger is pushed, is not the least. Indeed, it is essential that the drops have a predetermined volume which remains constant throughout the use of the device. The flow rate control filter which serves as a brake and prevents the evacuation of the medicinal substance in the form of a jet provides this regularity. This regularity is also obtained via the plunger in the form of a spring which constitutes a means to gear down its stroke relative to that of the piston. In practice, when the user pushes on the plunger, as a result of the elasticity of the spring, he can compress it by a certain length before causing the piston to move. The filter imposes a compression limit beyond which the substance penetrates through it to form a calibrated drop. Moreover, this filter also has an anti-particle function which prevents the passage of all solid particles coming from either the mixture of the medicine used to constitute the medicinal substance of the treatment, or the components of the device. Amongst the particles likely to come from the medicinal substance itself, there are particles which are poorly dissolved or poorly mixed during the manufacture of the product or particles resulting from polymerization which may take place during storage of the device.

Finally, certain substances cannot withstand high temperature sterilization, such that their preservation requires the introduction of at least one preservative during storage unless an aseptic filling is acceptable. A filter, or a pad specially designed to absorb this preservative before using the substance, may be inserted in the applicator nozzle. Indeed, these preservatives, which may give rise to allergies, cause irritations or side effects, must without fail be eliminated before introduction of the medicinal substance into the patient's eye.

The filter placed at the end of the applicator nozzle prevents contamination due to bacterial migration from the outside and spreading to the inside of the nozzle applicator. Finally, the mask fitted with a silver tip or any other appropriate material ensures permanent active disinfection of the distal end of the applicator nozzle.

The advantages for the manufacturer of the device represented by the realization illustrated in part by the FIGS. 4 to 7 in which the reservoir is lined can be seen in greater detail in FIGS. 12 to 20. These figures illustrate the whole of the manufacturing process of the device, i.e. the preparation and assembly of the various components.

FIG. 12 represents the phase which consists in cleaning and in coating in silicon, using retractable nozzles tips 60, the cylindrical jacket 40 held, throughout the operation, by a clip 61. This cylindrical jacket 40 is previously cut from a glass tube by thermal shock and undergoes no special transformation. This cylindrical jacket then undergoes refiring and depyrogenation at 300@C in a kiln 62 diagrammatically represented by FIG. 13. FIG. 14 illustrates the positioning of the movable sealing plug 30 using an axially mobile plunger 63. FIG. 15 represents the filling phase of the reservoir or more exactly of the jacket 40 by the medicinal substance 29 drawn in by a retractable injector 64. FIG. 16 represents the installation of the piston 12 via an axially mobile plunger 65. Given that the reservoir has a perfectly cylindrical external shape, a large quantity of these previously filled reservoirs can be placed alongside each other in a magazine 66 for subsequent processing. Among these later processes one of the most useful is autoclave sterilization which is practiced provided that the medicinal substance 29 can withstand the corresponding rise in temperature.

Figures 18, 19, 20:
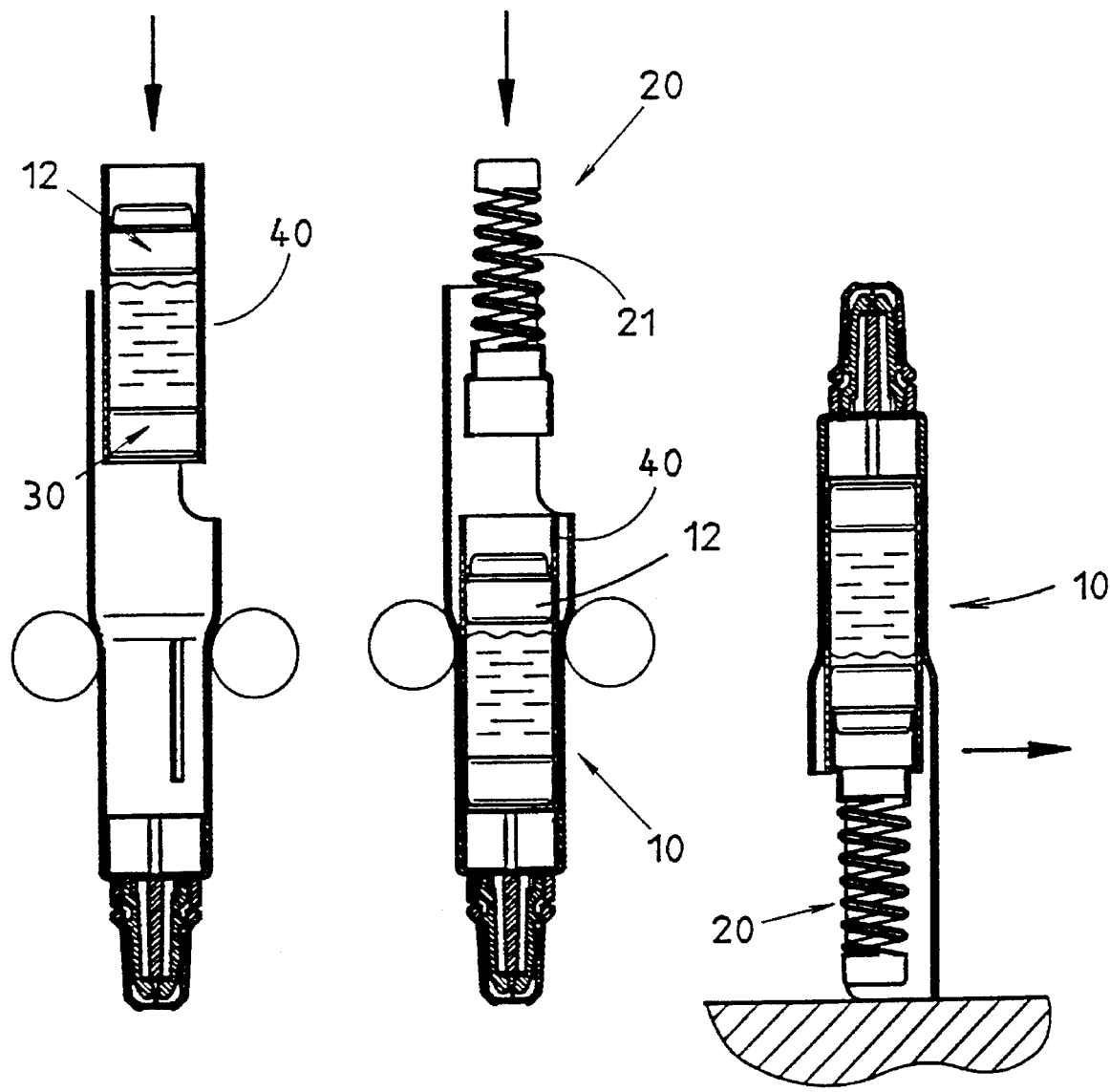

FIG. 18 illustrates the placing of the reservoir 10 in the device which has been previously sterilized in an appropriate manner. After this installation, the plunger 20 is brought into position and connected to the piston as is shown in FIG. 19. FIG. 20 shows the fully assembled and reversed device. In this position, it can also be stored in a magazine with a view to individual or collective packaging.

FIGS. 21 to 23 represent a storage and distribution device for eye drops in which the reservoir 10' is subdivided into two compartments 10'a and 10'b respectively, the lower compartment 10'a of which can contain either a lyophilisate 70 (as shown in the figure), or a powder, or a liquid and the upper compartment 10'b must contain a solvent 71 in the liquid state. As previously, the reservoir 10' is sealed at one of its ends by a movable sealing plug 30 and its upper end by a piston 12. An intermediate mobile plug 72 separates the two compartments 10'a and 10'b. In this form of realization, the cylindrical jacket 40 of the reservoir 10' presents in its central part an enlargement 73 which constitutes a by-pass when the system is used, which will be described below.

The other elements such as the plunger 20 and the applicator nozzle 14 are unchanged relative to those described above.

Activation of the device is illustrated by FIG. 22. A first thrust P1 on the plunger 20 causes the mobile intermediate plug 72 to move in the central area of the reservoir in which the cylindrical jacket contains the enlargement 73. As a result, the solvent 71 passes into the compartment 10'a to dissolve the powder or the lyophilisate 70. By this means, the medicinal substance is constituted or reconstituted which will be used subsequently to form the drops to be deposited in the patient's eye. The plunger 20 can be fitted with a movable stop in the form of a hood 74 limiting the stroke needed to mix these components.

The following phase, which is the utilization phase is illustrated by FIG. 23. At the end of the preceding phase, when all the solvent has passed into the compartment 10'a, the piston 20 is pushed up against the mobile intermediate seal 72 which now constitutes a single element functioning as a piston. After having withdrawn the movable stop, the operation of the device when in use is completely identical to that planned for a substance with a single component described previously. A thrust P2 on the piston, after preliminary evacuation of the gases contained in the bypass chamber has the effect of pushing the movable sealing plug 30 back into the bypass chamber 31 in so far as the said movable sealing plug has not already moved into the bypass chamber, then to enable the passage of the previously reconstituted medicinal substance to form the eye drops.

FIGS. 24 to 33 illustrate the various phases of preparation and assembly of the components of the previously described device in which the reservoir is of the two component mixture type. The first phase illustrated by FIG. 24 represents as before, the washing and coating with a silicon film of the jacket 40 previously cut out from a cylindrical glass tube, in which the enlargement 73 has been formed by a localized heating process enabling the appropriate deformation to be obtained. The following phase, represented by FIG. 25 consists in re-firing and depyrogenating this jacket in a kiln 62 at approximately 300@C. The following phase, represented by FIG. 26, is identical to that described with reference to FIG. 14. FIG. 27 consists in installing a first component which will subsequently undergo a lyophilization phase. This first component 70' will, after the lyophilization phase represented by FIG. 28, result in the lyophilisate 70 contained in compartment 10'a. It is to be noted that during the lyophilization phase the intermediate mobile plug 72 is prepositioned on the jacket 17. To enable the evacuation of the gases, the intermediate mobile seal 72 comprises at least one side vent 72' inserted for this purposes. During the following phase represented by FIG. 29, this intermediate mobile seal 72 is engaged in the cylindrical jacket 40 sufficiently to seal it.

Figures 30, 31, 32:
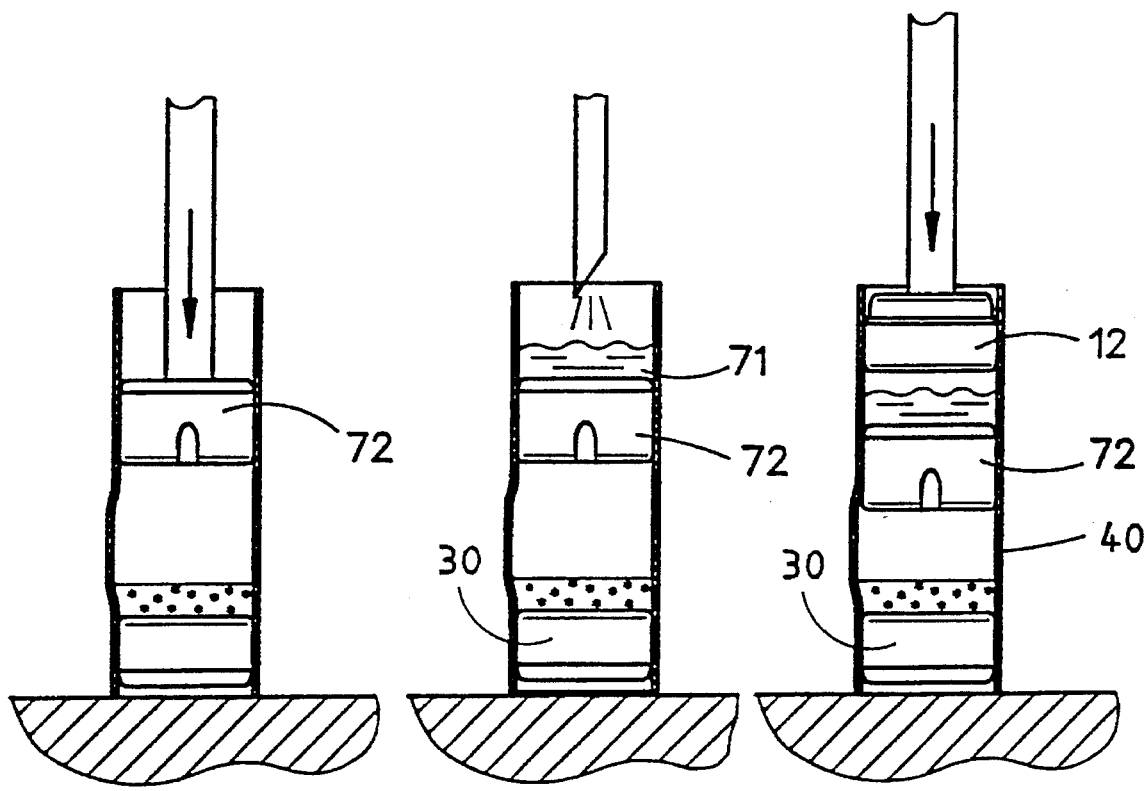
Figure 33:
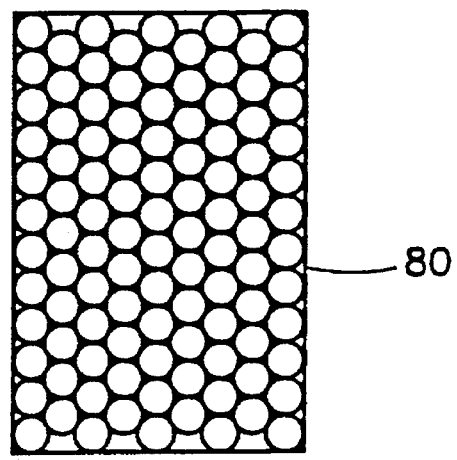

During the phase represented by FIG. 30, a plunger pushes the intermediate mobile seal 72 back into its central position which it will occupy during the storage phase of the device. After installation of this element, the solvent 71 is poured into the upper compartment formed at the bottom by the intermediate mobile seal. During the following phase represented by FIG. 32, the piston 20 is installed to ensure the final sealing of the cylindrical jacket 40. In this condition, the full reservoirs thus formed can be arranged in cassettes or magazines 80 (see FIG. 33) with a view to various treatments or various subsequent manipulations. It is clear that in this case a sterilization of the reservoirs is not possible given the existence of the lyophilisate which cannot withstand such an operation.

The installation of the reservoir in the body of the device and the assembly of the plunger when this reservoir is in place to make this device ready for storage, constitute identical operations to those described above with reference to FIGS. 18 to 20.

It was previously mentioned that the lyophilisate could be replaced either by a powder or by a liquid. Most of the operating phases designed to put the substances in the two compartments are identical to those described with reference to FIGS. 24 to 33. However, when one of the compartments contains a powder, it is necessary to first introduce the solvent into the upper compartment, then to position the intermediate mobile seal and finally to introduce the powder into the lower compartment. This inversion of the operations relative to those which consist in putting the lyophilisate and the solvent is made necessary in order to avoid contamination of the upper compartment by the powder. A reservoir decontamination phase is moreover required to eliminate the particles of powder which may have settled outside this reservoir. It should be noted that in this case, a sterilization is not generally possible because the powder is not able to withstand such an operation.

On the other hand, when the two substances contained respectively in the lower and the upper compartments are liquid solutions, the filling can be carried out either in one direction or in the other, i.e. it can be started either from the upper compartment or from the lower compartment. In addition, in so far as the solutions withstand a rise in temperature without any chemical transformation or decomposition, a total sterilization of the reservoir is possible.

The use in these two cases is identical to that described previously for the case where one of the compartments contains a lyophilisate.

For all these realizations, there may be the following problem. When the user pushes the piston, the compression of a small volume of air contained in the reservoir may, after deposition of an eye drop, push back a certain amount of liquid out of the applicator nozzle, with all the disadvantages which that may entail. In order to avoid this defect, a slight suction is created at the end of the use to suck back the amount of liquid which would tend to escape uncontrollably. This effect is obtained as a result of a special design of the piston 12. As is shown in FIG. 34, the piston 12 comprises a rigid retention stop 12a which is of one piece with the piston rod and a flexible ring shaped skirt 12b which goes around this stop. A supporting stud 12c is arranged at the base of the retention stop 12a such that at rest, the total height of the stop including the stud 12c corresponds approximately to that of the internal cavity 12d of the ring shaped skirt 12b. When the piston is pressed, the stud 12c causes a deformation in the base of the ring-shaped skirt as is shown in FIG. 35. After use, when the skirt returns to its original position, the depression created in the reservoir leads to a mini-aspiration, as is shown in FIG. 36. The objective is thus achieved.

With reference to FIG. 37, the device comprises a filter 90 mounted on the base of the applicator nozzle. This filter has a relatively large surface area. Inside the applicator nozzle a silver oxide sintered insert 91 is fitted which has a sterilizing function.

In the example represented by FIG. 38, the filter 92, which has advantageously sterilizing functions, has a smaller surface area. A silver insert 93 is advantageously placed inside the applicator nozzle. In both cases the insert defines an axial channel allowing the treatment substance to flow away.

FIG. 39 illustrates another form of realization which comprises a first tubular element 100 which is partially fitted into a second tubular element 101 with a closed bottom. The first tubular element is sealed by a fixed seal 102 arranged at one of the ends close to an applicator nozzle 103 of the device and by a mobile piston 104. The internal space inside this first tubular element and formed by the fixed seal 102 and the mobile piston 104 contains the medicinal substance. The second tubular element contains a sliding piston 105 which is mechanically linked to the mobile piston 104 by a hollow rigid element 106 defining a channel out of which the medicinal substance can flow.

The said first tubular element 100 is lodged in a capsule 107 which has at its end the applicator nozzle 103 capped by a movable protective hood 108. The said second tubular element 101 is capped with a hood 109 with a closed bottom which fits inside the capsule 107. This hood 109 comprises notches 110 or peripheral channels and the capsule comprises two or more elastic tongues 111 fitted with a spout designed to work in conjunction with the notches 110 to prevent the relative movement of the hood 109 outside the capsule whilst at the same time allowing movement in the opposite direction.

As is shown in FIGS. 40 and 41, to activate the device it is sufficient to push the second tubular element towards the first by pressing on the bottom of the hood 109. This has the effect of making the rigid element 106 move forwards, the tip 112 of this rigid element then passes through the mobile piston 104 in its pre-pierced central area, and push back the medicinal substance into a chamber which becomes free at the rear of the second tubular element 101 as a result of the movement of the sliding piston 105. Consequently, all the liquid substance is transferred from the front to the rear of the device. The mobile piston moves to the front and is blocked against the seal 102. The device is ready for use. An extra thrust on the bottom of the device causes the drop by drop flow of the medicinal substance.

FIG. 42 represents a variant of the device in accordance with FIGS. 39 to 41. In this realization a container 120 in which the medicinal substance is stored, is sealed by a sliding piston 121 and is engaged in a capsule 122 roughly similar to the capsule 107 of the device of the previous figures. The sliding piston 121 is mechanically linked with the capsule 122 by a rigid element 123 fixed on the bottom of this capsule and defining with the latter a central recess communicating with an applicator nozzle 124. A filter 125 and a silver cap 126 are fixed in this recess. The container contains a peripheral enlargement 127 which works in conjunction with the retention tongues 128 of one piece with the capsule 122 to retain the container within the capsule.

The detail of the shape of the sliding piston 121 is illustrated by FIGS. 43 and 44, during storage and during use respectively. It will be noted that the central part 121a of the sliding piston 121 is a membrane which loses its shape under the thrust from the end of the rigid element 123 during the utilization phase (FIG. 44), which has the effect of opening the unidirectional valve 121b and allowing the medicinal substance to flow through.

It can be seen that in all the forms of realization described and illustrated by the figures, there is to be found either in full or in part a certain number of means corresponding to the aims of the ideal device previously described in the specifications. Among these means there are means allowing the formation of eye drops with a constant force. These means comprise a mobile piston moving axially in the direction which renders it possible to create a drop in volume in a container in which the medicinal substance is stored or a fixed piston and a mobile container sliding above the fixed piston and ensuring a drop in volume of the chamber containing the medicinal substance stored in this mobile recipient.

There are also means which prevent the possibility of a vacuum being created inside the recipient. These means comprise a mobile piston and a piston rod which are not mechanically linked or a mobile piston with a unidirectional valve which is sealed when the mobile recipient withdraws, or a fixed seal with a unidirectional valve or a mobile plunger covering the mobile recipient without any link with the latter and preventing all possibility of withdrawing the mobile recipient by pulling on the latter, such that only a movement in one direction by thrust on the recipient is possible.

There are also means which make it possible to control the flow rate without risking forming a jet to generate regular precise drops. These means contain a flow rate controller creating a loss in load proportional to the pressure and viscosity of the solution in the form of a synthetic, porous depth filter, obtained for example by compressing powder or metal balls, then sintered in which calibrated holes or chicanes etc. . . . are pierced. This means is considered to be indispensable to obtain the desired result as it is impossible to control precisely the movement of the piston, movement which is in the order of one tenth of a millimetre to generate a drop of 30 μl., given the friction forces of the piston against the walls of the recipient. As soon as this friction force is overcome sliding is inevitable and the solution can flow out freely in the form of a jet in the absence of any flow rate controller.

It should be noted that this flow rate controller in a piston device has the same effect as that when pressure is exerted on the walls of a flexible container as is currently used in known devices.

It also has means enabling the elimination of residual pressure inside the recipient after the precise administration of a drop due to the movement of the piston, by generating residual pressure in the reservoir, pressure resulting from the friction force of the piston against the walls of the reservoir and the loss of load caused by the flow rate controller. These means are intended to avoid the creation of a second drop at the end of the applicator nozzle at the same time as the first drop. These means comprise a central area with the appearance of an elastic membrane placed in the centre of the sliding piston.

It also has means enabling the impenetrable sealing of the nozzle at its end, with guaranteed impenetrability and without generating excess pressure on or driving back the column of liquid in the applicator nozzle towards the inside of the recipient. These means comprise an unscrewed hood. In known systems the screwed hood is generally fitted with a sealing ring which seals the bottle before screwing the hood completely to avoid creating imperfect impenetrability due to the faulty tightening of this hood. This design presents the disadvantage that it generates excess pressure and causes the liquid column to be driven back towards the inside of the container, which is the cause of bacterial contamination or the creation of foam as a result of the penetration of air into the container.

It also has in addition means to eliminate turbulence in the applicator nozzle. Among such means there is a unidirectional valve and a unidirectional movement piston which prevents the aspiration of liquid back inside the container.

It also has means enabling the prevention of the migration of germs towards the inside of the nozzle applicator and towards the inside of the container. Among these means there is the presence of a sintered depth filter, chicanes, capillary openings, a sterilizing membrane filter, a porous ceramic filter or a filter in sintered glass.

It finally has means enabling the elimination of the proliferation of germs which may have migrated to the inside of the nozzle after the distribution of a drop. These means are obtained by the presence of materials having a bactericide or bacteriostatic auto-sterilizing action designed to inhibit the proliferation of the germs by an oligodynamic or a hydrolytic effect. These means comprise an element, a coating or an insert which can be porous or not made in heavy metals, for example precious or semi-precious metals such as for example silver, gold, platinum, tin, copper etc. . . . or in compounds of these metals, notably in oxides or mixtures of oxides such as silver oxide or in other materials such as ceramic, Teflon (R) or any other substance which has similar amorphous or hydrophobic effects, or finally a mixture or combination of above-mentioned metals, compounds or substances. Among these means there is also a special design of the applicator nozzle. This special design makes it possible to retain only an extremely small residual volume after formation and expulsion of a drop. In this context, it should be noted that the residual volume is ideally in the order of 10 to 20% of the volume of one drop, such that the loss remains minimal and the precision of dosage sufficiently large even when the oligodynamic effect denatures in part the active components of the residual volume mentioned above.

A preferred solution consists in inserting a porous rod inside the applicator nozzle, this rod being obtained by compression of silver oxide then sintered in order to provide a depth filter. In practice, the form giving the best results from the point of view of the microbiological results is that for which the surface area/volume ratio is as great as possible. The predetermined volume of medicinal substance situated in the distributor close to the orifice of the applicator nozzle is preferably less than the volume of a drop. The ratio between this predetermined volume measured in microlitres and the surface area of the asepticizing devices measured in square millimitres is in any case less than 1 and is preferably less than 0.5.

To summarize, as a result of the overall design of the device, and of its individual components and their interaction, a certain number of unique advantages are obtained both for the manufacturer and for the user.

With regard to use, given that the piston cannot be pushed forwards and can under no circumstances be drawn backwards, the aspiration of non sterile air back into the inside of the reservoir is totally impossible. Indeed, the plunger is simply fitted on the piston without being made solid with it. The filter constitutes a very effective aseptic barrier and finally the asepticizing devices guarantee the sterilization of any drops of substance which may remain in the applicator nozzle after initial use. As a result, the treatment substance remains sterile throughout the use of the device and thus as a result of the various methods described above it ought to be possible to ensure aseptic packaging of solutions which cannot undergo autoclave sterilization without making use of a preservative.

The piston is in addition manufactured such that after each use, it removes the residual pressure in the device, which prevents an undesirable flow of the medicinal substance. The problem of contamination due to penetration of germs after first use is solved thanks to the implementation of one or more elements having an oligodynamic effect. This effect, produced by different heavy metals or heavy metal oxides such as silver oxide, is well known. In order to be effective, the contact surface area of these asepticizing devices must be as large as possible for the smallest possible volume of medicinal substance to be treated. As a result, the volume to be treated, i.e. the residual volume remaining close to the orifice after depositing each drop, must be guaranteed to be constant and less than the volume of a drop. For this purpose it is preferable that an active element made in silver and sintered silver oxide, in the form of a depth filter, which may in addition act as a flow rate controlling device, be used.

I claim:

1. A device for storing a liquid medicinal substance and administering eye drops constituted by this substance, comprising a rigid cylindrical reservoir containing said substance and a distributor being connected to one end of said reservoir while the opposite end of said cylindrical reservoir being closed, said distributor having an applicator nozzle including an orifice designed to form and administer said drops to an eye of a patient, said distributor including a flow rate controlling device comprising at least one membrane with calibrated micropores which seals said reservoir, a sliding piston being engaged within said reservoir and being controlled by said device for dispensing liquid medicinal substance from said device, and said flow rate controlling device being connected to aseptization devices having an oligodynamic action on a predetermined volume of medicinal substance situated upstream from said orifice in which the piston contains a rigid retention stop and a flexible sheath defining an internal cavity, said retention stop comprises a supporting stud, and a total height of said stop with the supporting stud is roughly equal, at rest, to a height of the internal cavity.

2. A device in accordance with claim 1, wherein said flow rate controlling device comprising at least one membrane with calibrated micropores is located at a base of said distributor.

3. A device in accordance with claim 1, in which said sliding piston is connected with a hollow rigid element connected with a capsule, said cylindrical reservoir is at least partially inserted within said capsule, and said hollow element communicates with said distributor via at least one of a filter and said asepticizing devices.

4. A device in accordance with claim 3, in which the flow rate controlling device contains a depth filter made up of a sintered material containing at least one heavy metal having an oligodynamic anti-bacterial effect, chosen from the heavy metals, compounds and mixtures of heavy metals and mixtures of these compounds.

5. A device in accordance with claim 1, in which said asepticizing devices contain at least one of silver and silver oxide.

6. A device in accordance with claim 1, in which the predetermined volume is less than a volume of one drop.

7. A device in accordance with claim 6 in which a ratio between the predetermined volume measured in microlitres and a surface area of said asepticizing devices measured in square millimetres is less than 1.

8. A device in accordance with claim 1, in which said piston is provided with elastic devices arranged to absorb residual pressure.

9. A device in accordance with claim 8, in which said elastic devices contain a less resistant area installed on a piston side in contact with the medicinal substance and arranged to change shape under thrust exerted on said piston and to return to a normal state after conclusion of the thrust.

* * * * *